United States Patent
Nichols

(10) Patent No.: US 12,167,122 B2
(45) Date of Patent: Dec. 10, 2024

(54) PERSONAL CARE DEVICE WITH CAMERA

(71) Applicant: PREH HOLDING, LLC, Laguna Niguel, CA (US)

(72) Inventor: Thomas Nichols, Laguna Niguel, CA (US)

(73) Assignee: PREH Holding, LLC, Laguna Niguel, CA (US)

( * ) Notice: Subject to any disclaimer, the term of this patent is extended or adjusted under 35 U.S.C. 154(b) by 0 days.

(21) Appl. No.: 18/483,124

(22) Filed: Oct. 9, 2023

(65) Prior Publication Data

US 2024/0298086 A1     Sep. 5, 2024

Related U.S. Application Data

(63) Continuation of application No. 17/447,390, filed on Sep. 10, 2021, now Pat. No. 11,785,330, which is a
(Continued)

(51) Int. Cl.
| | |
|---|---|
| *H04N 23/63* | (2023.01) |
| *A46B 5/00* | (2006.01) |
| *A46B 9/02* | (2006.01) |
| *A46B 13/00* | (2006.01) |
| *A46B 15/00* | (2006.01) |

(Continued)

(52) U.S. Cl.
CPC ........... *H04N 23/63* (2023.01); *A46B 5/0095* (2013.01); *A46B 9/021* (2013.01); *A46B 13/008* (2013.01); *A46B 15/0004* (2013.01); *H04N 23/57* (2023.01); *H04N 23/69* (2023.01); *A45D 24/007* (2013.01); *A45D 2044/007* (2013.01);
(Continued)

(58) Field of Classification Search
CPC ........ H04N 23/63; H04N 23/57; H04N 23/69; A46B 5/0095; A46B 9/021; A46B 13/008; A46B 15/0004; A46B 2200/1006; A45D 24/007; A45D 2044/007; A45D 2200/205; A45D 2200/207
USPC ......................................................... 401/268
See application file for complete search history.

(56) References Cited

U.S. PATENT DOCUMENTS

| | | |
|---|---|---|
| D445,817 S | 7/2001 | Okuley |
| 6,340,677 B1 | 1/2002 | Nishimori et al. |

(Continued)

FOREIGN PATENT DOCUMENTS

| | | |
|---|---|---|
| JP | 2017-99428 A | 6/2017 |
| WO | WO 2014/147532 A1 | 9/2014 |

OTHER PUBLICATIONS

Canfield Scientific, Reveal Imager, website accessed dated Sep. 2, 2016.
(Continued)

*Primary Examiner* — Juan A Torres
(74) *Attorney, Agent, or Firm* — Knobbe, Martens, Olson & Bear, LLP

(57) ABSTRACT

A personal care system having a treatment device for applying a treatment to the skin or hair of a user is provided. The treatment device has a camera for taking an image of the skin. The system may include or be in communication with an application programming interface (API) that can process the image. The system or an associated API can recommend the use of treatment regimens or topical products according to information determined from the digital image of the skin.

20 Claims, 25 Drawing Sheets

Related U.S. Application Data continuation of application No. 16/734,194, filed on Jan. 3, 2020, now Pat. No. 11,122,206, which is a continuation-in-part of application No. 16/694,816, filed on Nov. 25, 2019, now abandoned, which is a continuation of application No. 15/462,509, filed on Mar. 17, 2017, now Pat. No. 10,511,777.

(60) Provisional application No. 62/472,368, filed on Mar. 16, 2017, provisional application No. 62/419,270, filed on Nov. 8, 2016, provisional application No. 62/845,598, filed on May 9, 2019, provisional application No. 62/954,333, filed on Dec. 27, 2019.

(51) Int. Cl.
*H04N 23/57* (2023.01)
*H04N 23/69* (2023.01)
*A45D 24/00* (2006.01)
*A45D 44/00* (2006.01)

(52) U.S. Cl.
CPC .. *A45D 2200/205* (2013.01); *A45D 2200/207* (2013.01); *A46B 2200/1006* (2013.01)

(56) References Cited

U.S. PATENT DOCUMENTS

| | | | |
|---|---|---|---|
| 6,734,858 B2 | 5/2004 | Attar et al. |
| 6,761,697 B2 | 7/2004 | Rubinstenn et al. |
| 6,907,193 B2 | 6/2005 | Kollias |
| 6,959,119 B2 | 10/2005 | Hawkins |
| 7,006,657 B2 | 2/2006 | Bazin |
| 7,104,800 B2 | 9/2006 | Ortiz-Valero et al. |
| 7,151,956 B2 | 12/2006 | Satoh et al. |
| D540,838 S | 4/2007 | Aronsson et al. |
| 7,220,254 B2 | 5/2007 | Altshuler et al. |
| 7,233,693 B2 | 6/2007 | Momma |
| 7,258,675 B2 | 8/2007 | Nichols |
| D552,809 S | 10/2007 | Linsbichler |
| 7,309,335 B2 | 12/2007 | Altshuler et al. |
| 7,317,818 B2 | 1/2008 | Lefebvre |
| 7,324,668 B2 | 1/2008 | Rubinstenn et al. |
| 7,454,046 B2 | 11/2008 | Chhibber et al. |
| 7,477,767 B2 | 1/2009 | Chhibber et al. |
| D589,650 S | 3/2009 | Adriaenssen |
| 7,564,990 B2 | 7/2009 | Kern et al. |
| 7,738,032 B2 | 6/2010 | Kollias et al. |
| 7,764,303 B2 | 7/2010 | Pote et al. |
| 7,856,118 B2 | 12/2010 | Kalla et al. |
| 7,894,651 B2 | 2/2011 | Gutkowicz-Krusin et al. |
| 7,953,613 B2 | 5/2011 | Gizewski |
| 7,986,987 B2 | 7/2011 | Bazin et al. |
| 8,026,942 B2 | 9/2011 | Payonk et al. |
| 8,027,505 B2 | 9/2011 | Edgar et al. |
| D649,636 S | 11/2011 | Bean et al. |
| 8,094,186 B2 | 1/2012 | Fukuoka et al. |
| 8,109,875 B2 | 2/2012 | Gizewski |
| 8,150,501 B2 | 4/2012 | Stamatas |
| 8,155,413 B2 | 4/2012 | Chhibber et al. |
| 8,157,753 B2 | 4/2012 | Nichols |
| 8,238,623 B2 | 8/2012 | Stephan et al. |
| 8,260,010 B2 | 9/2012 | Chhibber et al. |
| 8,360,973 B2 | 1/2013 | Bazin et al. |
| D675,829 S | 2/2013 | Jakubow |
| 8,373,859 B2 | 2/2013 | Chhibber et al. |
| 8,391,639 B2 | 3/2013 | Hillebrand et al. |
| 8,401,300 B2 | 3/2013 | Jiang et al. |
| 8,428,382 B2 | 4/2013 | Sato |
| 8,437,540 B2 | 5/2013 | Stephan et al. |
| 8,484,155 B2 | 7/2013 | Yamaguchi et al. |
| 8,532,736 B1 | 9/2013 | Malzbender et al. |
| D693,932 S | 11/2013 | Nichols |
| 8,591,414 B2 | 11/2013 | Kitamura et al. |
| 8,597,187 B2 | 12/2013 | Nuccitelli et al. |
| 8,611,588 B2 | 12/2013 | Kang |
| 8,620,421 B2 | 12/2013 | Yeo |
| 8,634,648 B2 | 1/2014 | Hyde et al. |
| D700,316 S | 2/2014 | Nichols |
| 8,644,615 B2 | 2/2014 | Hyde et al. |
| 8,652,042 B2 | 2/2014 | Mattoli et al. |
| 8,696,605 B2 | 4/2014 | Nichols |
| D713,971 S | 9/2014 | Nichols |
| 8,823,934 B2 | 9/2014 | Chhibber et al. |
| 8,837,796 B1 | 9/2014 | Zalutskaya |
| 8,855,751 B2 | 10/2014 | Kruglick |
| 8,861,863 B2 | 10/2014 | Chhibber et al. |
| 8,884,242 B2 | 11/2014 | Chhibber et al. |
| 8,915,562 B2 | 12/2014 | Edgar et al. |
| 8,941,727 B2 | 1/2015 | Rassman et al. |
| 8,965,081 B2 | 2/2015 | Nagase et al. |
| 9,075,003 B2 | 7/2015 | Oe et al. |
| D736,399 S | 8/2015 | Nichols |
| 9,101,320 B2 | 8/2015 | Cummins et al. |
| D738,508 S | 9/2015 | Nichols |
| 9,122,906 B2 | 9/2015 | Nakamura et al. |
| 9,138,257 B2 | 9/2015 | Revivo |
| D742,003 S | 10/2015 | Tasar |
| 9,189,679 B2 | 11/2015 | Yamazaki et al. |
| D747,800 S | 1/2016 | Dunleavy et al. |
| 9,247,802 B2 | 2/2016 | Edgar |
| 9,256,963 B2 | 2/2016 | Cummins et al. |
| 9,272,141 B2 | 3/2016 | Nichols |
| D753,400 S | 4/2016 | Khoun et al. |
| 9,326,685 B2 | 5/2016 | Krishnan et al. |
| 9,339,194 B2 | 5/2016 | Adams |
| 9,351,683 B2 | 5/2016 | Yoshida |
| 9,384,543 B2 | 7/2016 | Stephan et al. |
| D764,173 S | 8/2016 | Nichols |
| 9,402,546 B2 | 8/2016 | Segman |
| 9,414,780 B2 | 8/2016 | Rhoads |
| 9,427,187 B2 | 8/2016 | Gilbert |
| D765,982 S | 9/2016 | Nichols |
| D774,774 S | 12/2016 | Nichols |
| D780,245 S | 2/2017 | Ruback et al. |
| 9,579,250 B2 | 2/2017 | Nichols |
| D795,423 S | 8/2017 | Chen et al. |
| 9,730,758 B2 | 8/2017 | Carlucci |
| D799,711 S | 10/2017 | Sedic |
| D803,572 S | 11/2017 | Nichols |
| D805,571 S | 12/2017 | Hogstedt et al. |
| D805,572 S | 12/2017 | Hogstedt et al. |
| D813,203 S | 3/2018 | Hardi |
| D822,843 S | 7/2018 | Lenke |
| D825,188 S | 8/2018 | Luo |
| D830,700 S | 10/2018 | Xue |
| 10,252,051 B2 | 4/2019 | Nichols |
| D848,013 S | 5/2019 | Fuhner et al. |
| 10,285,624 B2 | 5/2019 | Taylor et al. |
| 10,307,098 B2 | 6/2019 | Gareau |
| 10,511,777 B2 | 12/2019 | Nichols |
| 11,122,206 B2 | 9/2021 | Nichols |
| 11,785,330 B2 | 10/2023 | Nichols |
| 2003/0012461 A1 | 1/2003 | Satoh et al. |
| 2004/0236254 A1 | 11/2004 | Nichols |
| 2009/0245603 A1* | 10/2009 | Koruga ............ A61B 5/444 382/128 |
| 2010/0139682 A1 | 6/2010 | Edgar et al. |
| 2010/0185064 A1 | 7/2010 | Bandic et al. |
| 2012/0008838 A1 | 1/2012 | Guyon et al. |
| 2012/0041282 A1 | 2/2012 | Nichol et al. |
| 2012/0041283 A1 | 2/2012 | Krishnan et al. |
| 2012/0041284 A1 | 2/2012 | Krishnan et al. |
| 2012/0307032 A1 | 12/2012 | Gomi et al. |
| 2013/0046212 A1 | 2/2013 | Nichols |
| 2013/0060176 A1 | 3/2013 | Nichols |
| 2013/0197397 A1 | 8/2013 | Waugh et al. |
| 2014/0194790 A1 | 7/2014 | Crunick et al. |
| 2014/0314315 A1 | 10/2014 | Chhibber et al. |
| 2014/0350409 A1 | 11/2014 | Chhibber et al. |
| 2015/0086104 A1 | 3/2015 | Miyamoto et al. |
| 2015/0099947 A1 | 4/2015 | Qu et al. |
| 2015/0105635 A1 | 4/2015 | Yoshida et al. |
| 2015/0173842 A1 | 6/2015 | Carlucci |

(56) References Cited

U.S. PATENT DOCUMENTS

| | | |
|---|---|---|
| 2015/0182757 A1 | 7/2015 | Levine et al. |
| 2015/0223749 A1 | 8/2015 | Park et al. |
| 2015/0254847 A1 | 9/2015 | Nakamura et al. |
| 2015/0287190 A1 | 10/2015 | Kim et al. |
| 2015/0287191 A1 | 10/2015 | Koruga et al. |
| 2015/0342515 A1 | 12/2015 | Hutchings et al. |
| 2015/0346936 A1 | 12/2015 | Rodan et al. |
| 2016/0007908 A1 | 1/2016 | Guo |
| 2016/0022008 A1 | 1/2016 | Rabe et al. |
| 2016/0022009 A1 | 1/2016 | Rabe et al. |
| 2016/0022010 A1 | 1/2016 | Rabe et al. |
| 2016/0022011 A1 | 1/2016 | Rabe et al. |
| 2016/0081553 A1 | 3/2016 | Weber et al. |
| 2016/0154992 A1 | 6/2016 | Shinoda et al. |
| 2016/0213126 A1 | 7/2016 | Chang |
| 2016/0262624 A1 | 9/2016 | Nakajima et al. |
| 2017/0115726 A1 | 4/2017 | Fung |
| 2017/0150851 A1 | 6/2017 | Sueyoshi et al. |
| 2017/0202732 A1 | 7/2017 | Nichols |
| 2017/0270593 A1* | 9/2017 | Sherman ............ G06Q 30/0251 |
| 2017/0367543 A1* | 12/2017 | Straka .................... A61H 7/005 |
| 2018/0125201 A1 | 5/2018 | Nichols |
| 2018/0279762 A1 | 10/2018 | Park et al. |
| 2020/0280680 A1 | 9/2020 | Nichols |
| 2022/0210332 A1 | 6/2022 | Nichols |

OTHER PUBLICATIONS

Canfield Scientific, VISIA, website accessed dated Sep. 2, 2016.
Salzano, Megan. "Philips Develops Connected Home Health Care System." Homeworld Business. Dated Sep. 12, 2016. 111-112.
Stella, Rick, "Onvi's Smart Toothbrush Features a Live Video Feed of Your Mouth While You Brush." Digital Trends, Dated May 19, 2016 (accessed Aug. 28, 2019 using the internet archive way back machine).
International Search Report and Written Opinion for Application No. PCT/US2020/031717 dated Jul. 30, 2020 in 6 pages.

* cited by examiner

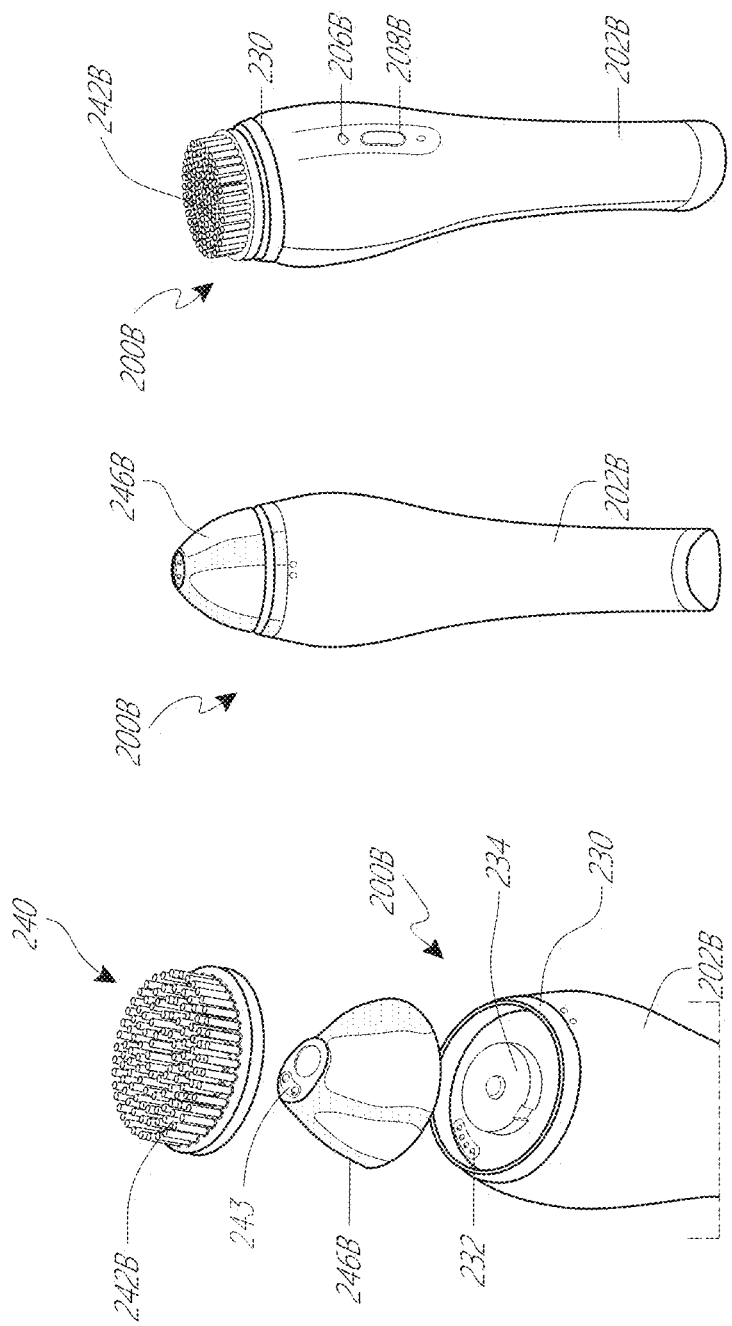

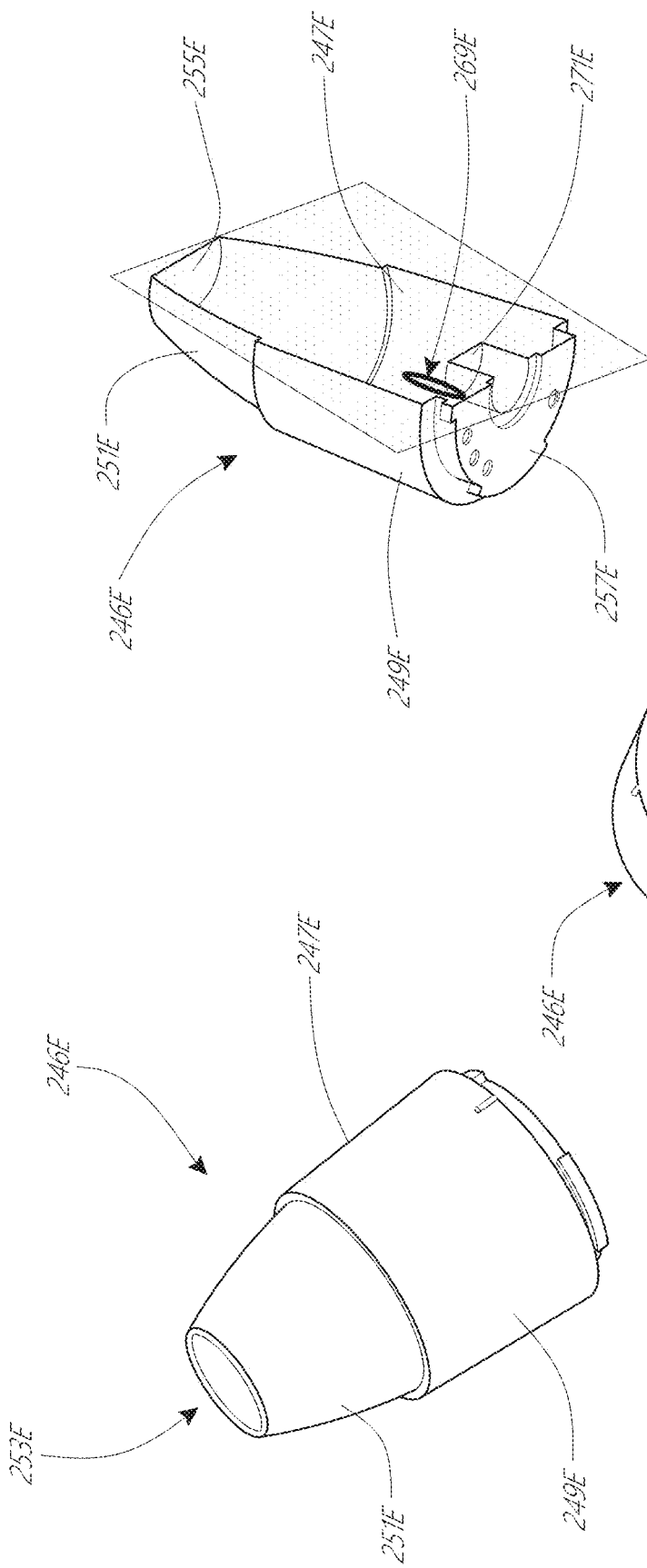
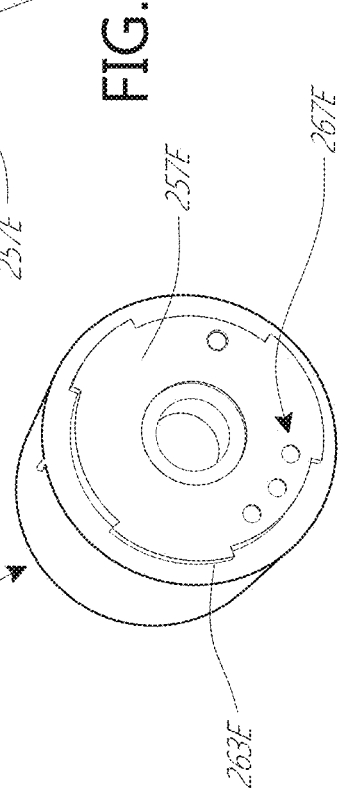
FIG. 13A
FIG. 13B
FIG. 13C

PERSONAL CARE DEVICE WITH CAMERA

INCORPORATION BY REFERENCE TO ANY PRIORITY APPLICATIONS

This application is a continuation of application of U.S. patent application Ser. No. 17/447,390, filed Sep. 10, 2021, which is a continuation of application of U.S. patent application Ser. No. 16/734,194, filed Jan. 3, 2020, which is a continuation-in-part of application of U.S. patent application Ser. No. 16/694,816, filed Nov. 25, 2019, which is a continuation of U.S. patent application Ser. No. 15/462,509, filed Mar. 17, 2017, now issued as U.S. Pat. No. 10,511,777, which claims priority to provisional U.S. Application No. 62/419,270, filed Nov. 8, 2016, and to provisional U.S. Application No. 62/472,368, filed Mar. 16, 2017. U.S. patent application Ser. No. 16/734,194 also claims priority to provisional U.S. Application No. 62/845,598, filed May 9, 2019, and to provisional U.S. Application No. 62/954,333, filed Dec. 27, 2019. The disclosures of all of these prior applications are hereby incorporated by reference herein in their entirety and should be considered a part of this specification for all purposes. Any and all applications for which a foreign or domestic priority claim is identified in the Application Data Sheet as filed with the present application are hereby incorporated by reference under 37 CFR 1.57.

BACKGROUND

Field

This application relates, in general, to a personal care device with an imaging device, and in one arrangement, to a personal skin care device with a camera.

Description of the Related Art

There exist various personal skin care devices. Such devices include facial brushes which can be used to remove cell debris, exfoliate and resurface skin for reduced fine lines, wrinkles and pore size and can prepare the skin to better absorb skin care treatments. Such facial brushes can be used separately or in combination with skin care treatments.

SUMMARY

The systems, methods and devices described herein have innovative aspects, no single one of which is indispensable or solely responsible for their desirable attributes. Without limiting the scope of the claims, some of the advantageous features will now be summarized.

The present application typically describes devices, systems, and methods for personal grooming, and more specifically for caring for skin or hair. In accordance with certain aspects of the present disclosure, there is provided a personal care system that includes a handheld treatment device. The device has a treatment head that applies a treatment to a skin of a user. The device has a camera that takes digital images of the skin. The system has an application programming interface (API) that allows the user to capture images of the skin with the camera and use the images to recommend or adjust the use of a skin care device.

Another aspect of the present disclosure is a method of treating skin. The method includes applying a treatment to the skin with a handheld treatment device and acquiring an image of the skin with a camera attached to the handheld treatment device. The method further includes processing the image of the skin with an API.

In some aspects, a personal care system is disclosed. The personal care system includes a handheld treatment device, a treatment head, a camera, and optionally an application programming interface (API) implemented within the handheld treatment device or by a mobile computing device or server in communication with the handheld treatment device. The treatment head is disposed on the treatment device and configured to apply a treatment to a skin of a user. The camera is disposed on the treatment device. The API allows the user to capture one or more images of the skin, then the API or an associated component or module may analyze said one or more images to recommend or adjust the use of a skin care device.

The personal care system of the preceding paragraph can further include one or more of the following features: The camera is a detachable camera that can be removed from the treatment device. The detachable camera includes a housing. The housing circumferentially surrounds a focusing lens. The focusing lens is longitudinally spaced apart from a camera lens by a distance equal to a focal length of the focusing lens. The detachable camera includes the camera lens. The detachable camera further includes a light source that is circumferentially surrounded by the housing. Each of the camera and the treatment head can be reversibly coupled to a platform disposed on the handheld treatment device. The handheld treatment device can be selected from the group consisting of a facial brush, a micro current device, a LED light device and an ultrasound device. The API can recommend a topical skin care product. The camera can acquire the one or more images at a magnification of 10× to 400×. The personal care system is used in combination with a display for displaying images captured by the camera. The display includes a foldable handle. The foldable handle extends from a back surface of the display. The foldable handle is movable between a first configuration and a second configuration. The foldable handle is substantially parallel with a screen of the display in the first configuration. The foldable handle forms an angle with the screen in the second configuration. The angle is between 20 degrees and 80 degrees.

In some aspects, a method of treating a skin is disclosed. The method includes applying a treatment to the skin with a handheld treatment device; acquiring an image of the skin with a camera attached to the handheld treatment device; and processing the image, such as with an application programming interface (API) configured to perform automated image analysis with respect to the acquired image.

The method of the preceding paragraph can further include one or more of the following features: The step of acquiring an image of the skin includes acquiring a first image before applying the treatment to the skin; and acquiring a second image after applying the treatment to the skin. The method further includes the steps of attaching a treatment head to the handheld treatment device before applying the treatment to the skin; removing the treatment head from the handheld treatment device after applying the treatment to the skin; and attaching the camera to the handheld treatment device after removing the treatment head from the handheld treatment device.

In some aspects, a personal care device is disclosed. The device includes a handle portion, a head portion, a treatment head, and a lens module. The head portion is disposed at an end of the handle portion and includes a platform. The treatment head extends away from the platform along a first direction of a longitudinal axis of the head portion. The lens module is positioned within the head portion and includes a compartment that is enclosed by a cover and a housing of the head portion. The lens module further includes a camera lens and a light source that are each disposed within the compartment. The camera lens faces away from the platform along a second direction of the longitudinal axis, the second direction being oriented opposite the first direction.

The device of the preceding paragraph can further include one or more of the following features: the treatment head is reversibly detachable from the platform; the treatment head is selected from the group consisting of a facial brush, a micro current device, a LED light device, and an ultrasound device; the light source is a LED light; the device further comprises a sensor disposed on the head portion.

In some aspects, a personal care device is disclosed. The device includes a handle portion, a head portion, a treatment head, and a controller. The head portion includes a grip portion that extends along a first longitudinal direction. The head portion is positioned at an end of the handle portion and includes a platform. The treatment head is coupled to the platform and extends away from the platform in a first direction along a second longitudinal axis that is transverse to the first longitudinal axis. The controller is disposed on the handle portion and oriented to face toward the first direction. The controller is disposed on a medial plane of the handle portion such that the controller is centered relative to the treatment head when the device is viewed facing the controller.

The device of the preceding paragraph can further include one or more of the following features: the device further comprises a lens module positioned within the head portion, the lens module extending away from the platform along the second longitudinal in a direction opposite the first direction; the treatment head is selected from the group consisting of a facial brush, a micro current device, a LED light device, and an ultrasound device; the light source is a LED light; the device further comprises a sensor disposed on the head portion.

In some aspects, a personal care device is disclosed. The device includes a handle portion, a head portion, a treatment head, a lens module, a camera controller button, and an indicator. The head portion is positioned at an end of the handle portion and includes a platform. The treatment head extends from the platform along a first direction of a longitudinal axis of the platform when the treatment head is coupled to the platform. The lens module is positioned within the head portion and includes a camera lens facing away from the platform along a second direction of the longitudinal axis, the second direction being opposite the first direction. The camera controller button is disposed on the handle portion and faces toward the second direction. The indicator is disposed on the handle portion and between the camera controller and the camera lens.

The device of the preceding paragraph can further include one or more of the following features: the indicator is configured to allow a user to aim the camera lens based on feeling the orientation of the indicator relative to the camera controller button; the lens module comprises a compartment that is enclosed by a cover and a housing of the head portion, the camera lens disposed within the compartment; the device further comprises a sensor disposed on the head portion.

In some aspects, a personal care device is disclosed. The device includes a handle portion, a head portion, a treatment head, a lens module, and a sensor. The head portion is disposed at an end of the handle portion and includes a platform. The treatment head extends from the platform along a first direction of a longitudinal axis of the platform when the treatment head is coupled to the platform. The lens module is positioned within the head portion and includes a lens module facing away from the platform along a second direction of the longitudinal axis, the second direction being opposite the first direction. The sensor is disposed on the head portion and is configured to measure a characteristic of a skin.

The device of the preceding paragraph can further include one or more of the following features: the characteristic measured by the sensor is selected from the group consisting of: a moisture content, a pore size, a pore count, a sebum amount, a sebum composition, an elasticity, a fine line count, a fine line branching, a wrinkle count, and a wrinkle depth; the device is in contact with the skin when the sensor measures the characteristic of the skin; the device is spaced apart from the skin when the sensor measures the characteristic of the skin.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 5C shows an embodiment of a treatment device having detachable treatment heads.

FIG. 5D shows the treatment device of FIG. 5C with a detachable camera attached to the treatment device.

FIG. 5E shows the treatment device of FIG. 5C with a brush attached to the treatment device.

FIG. 13A shows a side view of the detachable camera of FIG. 10A.

FIG. 13B shows a bottom view of the detachable camera of FIG. 13A.

FIG. 13C shows a cross-sectional side view of the detachable camera of FIG. 13A.

DETAILED DESCRIPTION

Figure 1:
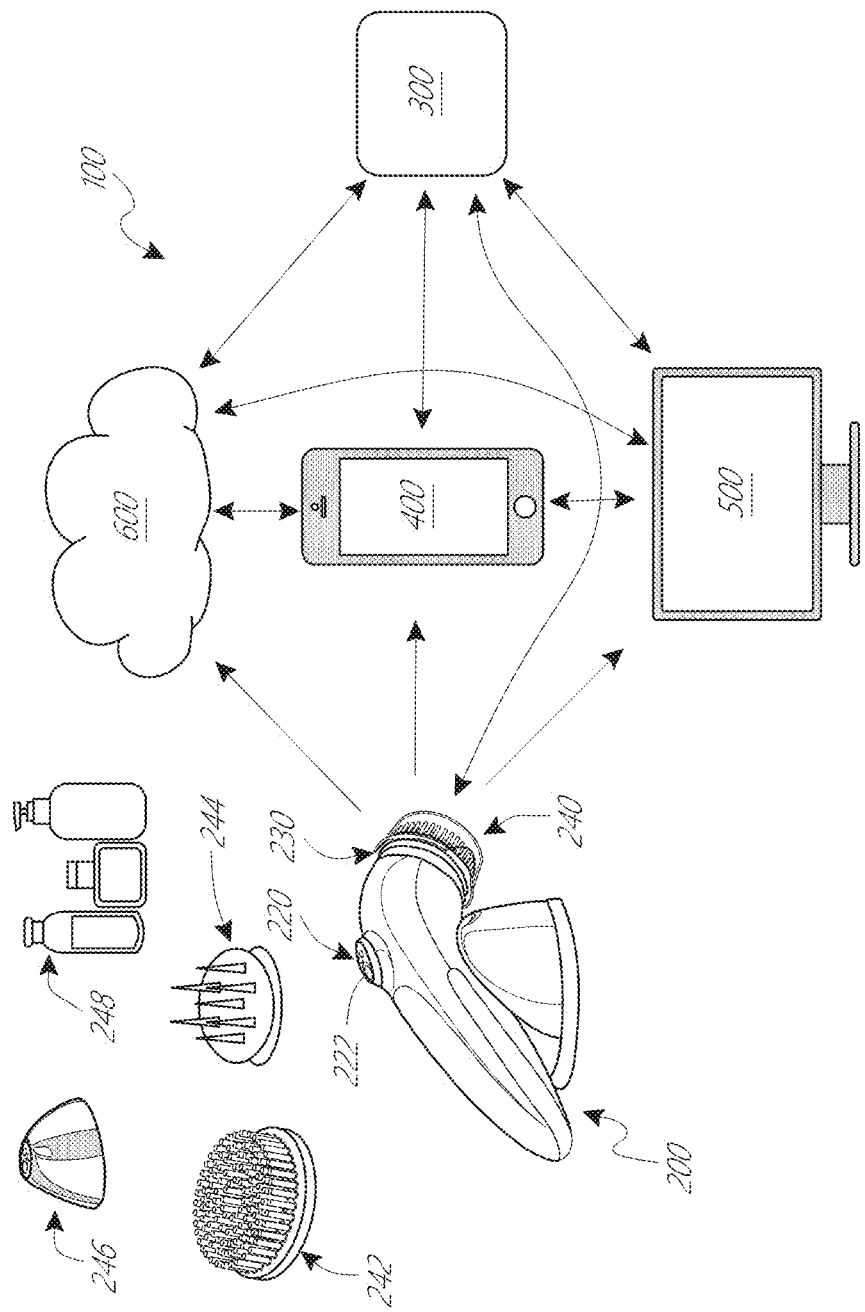
FIG. 1 shows an embodiment of a personal care system.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Most people use personal care products to give themselves an aesthetically-pleasing external appearance. Personal care products can include skin and hair care products such as, for example, cleansing brushes, exfoliating pads, electrical energy therapy devices, pulsed-light therapy devices, acoustical energy therapy devices, hair shampoos and conditioners, cosmetics, and skin lotions. Many of these products can be used in different operational modes. For example, a skin-cleansing brush can be used on a device that spins the brush at a high-speed, at a low-speed, in an oscillatory mode, or in other some combination of these modes. Personal care products can be used with other personal care products. For example, a microcurrent therapy device can be used to increase skin absorption of a lotion. Thus, consumers can have a wide variety of personal care treatment regimens from which they can select when they are seeking to manage the care of their skin and/or hair. An aspect of the present disclosure is the recognition that there is a need for a device that can help a consumer select or monitor a use of a personal care treatment product and/or treatment regimen.

FIG. 1 shows an embodiment of a personal care system 100 of the present disclosure. The personal care system 100 can be a home-use skin treatment system. The system 100 can include a treatment device 200. The treatment device 200 can be a hand-held personal care device, such as, for example a facial beauty device or hair apparatus. The treatment device 200 can include a platform 230 that allows a treatment head 240 to be attached to the device 200. As discussed below, the platform 230 can be adapted so that different treatment heads 240 can be attached and removed from the device 200. In some embodiments, the treatment head 240 cannot be removed from the platform 230 without destroying the device 200. The device 200 can include a camera 220 that is disposed on or contained within the device 200. The camera 220 can be a fixed camera 222 that is bonded or otherwise fixedly attached to the treatment device 200. In some arrangements, the camera 220 can be a detachable camera 246 that can be reversibly attached to the treatment device 200. The detachable camera 246 can attach to the device 200 at the platform 230. The platform 230 can be configured so that either a detachable camera 246 or a treatment head 240 can be attached to the device 200 at the platform 230. As discussed below, a user can attach a treatment head 240 to the device 200 at the platform 230, treat the skin with the device 200 using the treatment head 240, remove the treatment head 240 from the platform 230, attach a detachable camera 246 to the device 200 at the platform 230, and take images of the skin with the detachable camera 246 to see how well the treatment head 240 treated the skin. The system 100 can process images from the camera 220 to allow a user to assess a condition of the skin or hair, as described in more detail below.

In certain arrangements, the device 200 can be waterproof or water-resistant, allowing the device 200 to be submerged or brought into contact with water without damaging the device 200. The device 200 can be adapted to allow a user to use the device 200 in a shower or a bathtub. The housing of the device 200 can form a water-tight seal that prevents water from entering the internal space of the device 200, thereby protecting the internal electronics of the device 200 from being contacted by water. The housing of the device 200 can form a water-tight seal with the platform 230 and the fixed camera 222. The fixed camera 222 can be waterproof or water-resistant, allowing the device 200 to be used in a shower or a bathtub.

In some arrangements, the device includes the detachable camera 246 and does not include the fixed camera 222, thereby reducing the need to make a water-tight seal for the fixed camera 222. For example, the platform 230 can be waterproof or water-resistant, allowing the device to be submerged in water when a treatment head is attached to the platform 230. The detachable camera 246, however, need not be waterproof or water-resistant, allowing the user to use the detachable camera 246 only under non-washing conditions. For example, a treatment head 240 can be attached to the platform 230, which forms a water-tight seal with the device 200, and used to administer a cleansing treatment to the skin of the user. The device 200 can be submerged or brought into contact with water without damaging the device 200 during use of the device 200 with the treatment head 240 attached to the device 200. Under non-washing (e.g., dry) conditions, the detachable camera 246 can be attached to the platform 230 and used to image the skin of the user. The housing of the detachable camera 246 need not be, but can be, waterproof or water-resistant. A detachable camera 246 that does not require a water-proof or water-resistant camera housing may reduce manufacturing costs of the device 200 compared with a device 200 having a fixed camera 222 that requires a waterproof or water-resistant camera housing.

The system 100 can be controlled or monitored by a mobile or pad device (such as a mobile phone, tablet device, laptop computer, etc.). The system 100 can include an application programming interface (API) 300. The API 300 can be implemented within or called by a software application (sometimes referred to herein as a mobile application, though it will be appreciated that such functionality need not be provided for use on a mobile device specifically, or even by a dedicated application, depending on the embodiment) that is downloaded onto a mobile phone 400 or other home computing device (e.g., tablet, personal computer). It will be appreciated that the device 200, mobile device 400 and/or a remote system or server may communicate with each other via specialized API calls that enable one of the devices or systems to request that another device or system generate responsive data to be returned via an API response. For example, the device 200 may send API requests or responses to the mobile device 400 (such as via Bluetooth or wireless network communication) and/or to a remote server 600 (such as via the Internet or other network), and the mobile device 400 may send API requests or responses to the device 200 or the server 600. It will be appreciated that particular aspects or functionality of the API described herein may be implemented at different devices or systems illustrated in FIG. 1. For example, the mobile device 400 may implement aspects of the API related to generating user interfaces that display images captured by the device 200, while a server 600 may implement aspects of the API that employ one or more machine learning models to analyze images provided to the server by the device 200 or mobile device 400. The particular device or system that implements particular functionality described herein, such as functionality or features described herein as being provided by the API 300, may depend on the processing capabilities of the given device in the given embodiment. For example, a mobile application described herein may be configured to execute image analysis locally or to request that such image analysis be performed remotely at a server depending on the processing capabilities of a particular mobile phone or tablet on which the mobile application is operating.

In some embodiments, the system 100 can be controlled or monitored by an application that is executed on the mobile or pad device 400. The system 100 can include a display 500. In some embodiments, the display 500 can include a processor and a memory storage onto which components implementing (or configured to access) aspects of the API 300 are installed. The display 500 can be an LCD monitor. The display can be adapted to sit on a vanity. The system 100 can be used in a home, a salon, or a retail cosmetics counter. The display 500 can be waterproof or water-resistant. The display 500 can be a touchscreen display. The display 500 can present a graphic user interface (GUI) or other user interface that allows a user to interact with other components of the system 100 (e.g., the API 300). In some embodiments, such a GUI or other user interface may be generated by the mobile device 400 (such as by an application operated thereon) or the device 200, then communicated to the display 500 for visual presentation to a user (such as in embodiments in which no specialized software or components are installed on the display 500). The display 500 can include control buttons or other input devices that allow a user to interact with other components of the system 100 through the display 500.

As discussed below, the API 300 in whole or in part can be executed on or implemented by one or more of the treatment device 200, the mobile phone 400 or other home computing device, and/or the display 500. The mobile application and/or the API 300 can provide the following functionalities, in some embodiments: power on or off the system 100; take before and after images; instruct the user how to perform functions of the system 100 (e.g., take images, store or access image files, schedule treatment regimens); display images singularly or side-by-side; calculate and monitor user measurements (e.g., wrinkle depth, fine line frequency, epidermal layer exfoliation, skin hydration); and/or provide detailed images for evaluation. The API 300 and software updates to the API 300 can be downloaded from the internet. In some arrangements, the API 300 or software configured to access the API 300 comes already installed onto one of the components of the system 100, such as, for example, the display 500. As shown in FIG. 1, the system 100 can include components that communicate with a network of servers 600. The network of servers 600 can herein be referred to as "the cloud." One or more components of the system 100 (e.g., the device 200, the mobile phone 400, the display 500) can communicate with one another wirelessly (e.g., Wi-Fi, Bluetooth) or through wired connections.

With continued reference to FIG. 1, the device 200 can include a treatment head 240. The treatment head 240 can include a brush 242, an energy-delivery applicator 244, a camera 246, and/or combinations thereof. The energy-delivery applicator 244 can be, for example, a micro-current applicator, a LED light applicator, an impulsed light applicator, a heat applicator, an ultrasound applicator, and/or combinations thereof. The treatment head 240 can be a facial scrubbing brush or a makeup remover pad. The treatment head 240 can apply micro current for wrinkle reduction or LED light for wrinkle reduction and treatment of acne. The treatment head 240 can apply ultrasound for infusing. The treatment head 240 can be a micro-pulsating infuser to enhance skin absorption. The treatment head 240 can apply impulse light for hair removal or hair growth. The treatment head 240 can apply high-frequency vibration to exfoliate.

The treatment head 240 can be fixedly attached to the device such that the treatment head 240 cannot be removed from the device 200 without destroying the device 200. In some arrangements, the treatment head 240 can be reversibly attached to the device 200. In certain configurations, the device 200 can receive a variety of different detachable treatment heads 240 thereby allowing a user to remove a first treatment head 240 from the device 200 and attach a different treatment head 240 to the device 200. For example, a user can use the device 200 with a removable brush 242 attached to the device 200. The user can then remove the detachable brush 242 from the device 200 and attach a detachable camera 246 and take a digital image of the user's skin to see how well the brush 242 cleaned the user's skin.

The system 100 can process images from the camera 220. In some arrangements, the API 300 can be used for capturing an image with the camera 220. The API 300 can be used to process images, such as, for example, an image of the consumer's skin. The API 300 can be used to process images captured by the camera 220. The API 300 can be external to and in communication with the device 200. In some arrangements, the API 300 can be included within the device 200. In certain configurations, the system 100 can include a device 200 that includes a camera 220 and an API 300 within the device 200. The camera 220 can use the API 300 to link via Wi-Fi or Bluetooth to the mobile device 400, the display 500, the cloud 600, or combinations thereof. The API 300 can provide images captured by a fixed camera 222 or a detachable camera 246 to the mobile device 400, the display 500, the cloud 600, or combinations thereof. The API 300 can allow a user to program or control the operation of the device 200. In some arrangements, the API 300 can allow a user to use a GUI of the display 500 or the mobile phone 400 to program or control the operation of the device 200. For example, the API 300 can allow a user to use the mobile phone 400 to program the speed at which, and/or the duration of time, the device 200 rotates a brush that is attached to the treatment head 240 of the device 200. The API 300 can allow a user to schedule or program treatment regimens. The device 200 can recognize the treatment head 240 attached to the device 200 and can alert a user if an improper treatment head 240 is attached to the device 200.

As discussed above, the camera 220 and the API 300 can allow a user to digitally photograph a section of skin. The system 100 can allow a user to acquire a digital image of skin at an increased magnification. For example, the system 100 can allow a user to photograph a section of skin at a magnification of about: 2×, 10×, 50×, 400×, and values therebetween. In some arrangements, the system 100 includes a camera 220 that includes a zoom-in feature that increases the magnification of the camera 220. In certain configurations, the system 100 can have a device 200 that can receive different detachable cameras 246, allowing a user to exchange the different detachable cameras 246 in order to acquire images at different magnifications. For example, a user can attach a first detachable camera 246 to the device 200 to acquire an image of the skin at a magnification of about 50×. The user can then remove the first detachable camera 246 from the device 200 and attach a second detachable camera 246 to acquire an image of the skin at a magnification of about 400×.

A user may acquire digital photographs that one or more devices of system 100 analyze to determine information relating to a condition of the skin, such as, for example, depth of fine lines and wrinkles, moisture and oil levels within the skin, and/or debris of the epidermis. In some arrangements, a user may acquire images of the skin at 2× to 400× magnification to enhance the accuracy of the system 100 in determining information relating to a condition of the skin such as, for example, depth of fine lines and wrinkles, moisture and oil levels within the skin, and/or debris of the epidermis.

The system 100 can allow a user to acquire images of the skin before and/or after a treatment of the skin. The system 100 can enable "before-and-after" visual results, which may be presented via a user interface displayed by the mobile device 400, device 200, or display 500. For example, a user can take a "before" image before treating the skin, then treat the skin, and then take an "after" image of the skin. The treatment administered to the skin can be administered by the device 200. The system 100 can allow a user to evaluate a treatment administered to the skin. For example, a user can use the system 100 to take a series of images of the skin over the course of time (e.g., over days, weeks, months) and compare the images to one another to evaluate whether a treatment regimen applied to the skin is effective at improving a skin condition (e.g., wrinkle reduction).

The API 300 can help a user manage the images that are acquired with the device 200. For example, the API 300 can allow a user to view, organize, and archive the images a user takes with the system 100. The API 300 can capture and store images and build records. The API 300 can track how often and how well each treatment improves a condition of the skin. The API 300 can look at trends in the skin condition over time. The API 300 can provide the user easy-to-follow tips to improve preventative and daily skin care habits. The API 300 can be used to transfer the images between one or more of the mobile device 400, the display 500, and the cloud 600. The API 300 can tag information associated with the image such as the date and/or time that the image was acquired, which may be stored as image metadata associated with a stored image file. The API 300 can tag the image with information about how the device 200 was used immediately before the image was acquired. The API 300 can track the operational modes of the device 200 with the resulting images. For example, images that indicate skin irritation can be correlated with the operational modes of the device 200 that preceded the image such that the API 300 can recommend a change in the treatment regimen applied to the skin by the device 200. The API 300 can allow a user to tailor the operational mode of the device 200 according to the skin sensitivity or skin condition of the user. In some arrangements, the API 300 can take information detail from the digital image and provide the user with corrective information. The API 300 can provide a user with guidance on how the device 200 can be used to improve the condition of the skin. For example, the API 300 can recommend a type of brush 242 or energy-delivery applicator 244 to use on the device 200, an operational mode for using the device 200, and/or a lotion or topical skin product 248 to incorporate for use in combination with the device 200.

The API 300 and the camera 220 can be incorporated into a device 200 such as a rotatable brush such as a Sonic Dermabrasion brush from PRETIKA™. The API 300 and the camera 222 can be incorporated into existing personal care devices known in the art such as a MicroCurrent device, a LED light device, or an Ultrasonic device.

The system 100 can allow the user to watch live digital image and/or video feed on a mobile device 400 or display 500 during use of the device 200. The system 100 can allow users to see before and after results in real-time on a display 500 that is a small LCD monitor that is included with the device 200. In some arrangements, the system 100 does not include a display 500 with the device 200 and can allow users to see before and after results in real-time on a mobile device 400. The system 100 can wirelessly synch the device 200 with one or more of the cloud 600, the mobile device 400, and the display 500 using Bluetooth and Wi-Fi. The device 200 and the display 500 can include a USB charger to charge the device 200 and/or the display 500. The USB charger can charge and/or transfer data to or from the device 200 and the display 500.

Figure 2B:
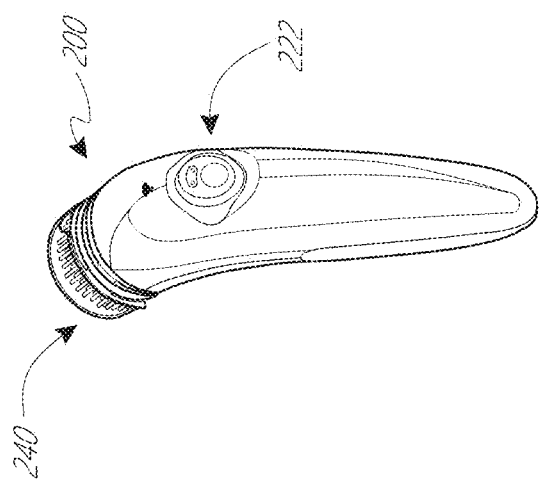
FIG. 2B shows a partial rear view of the treatment device of FIG. 2A.
Figure 2A:
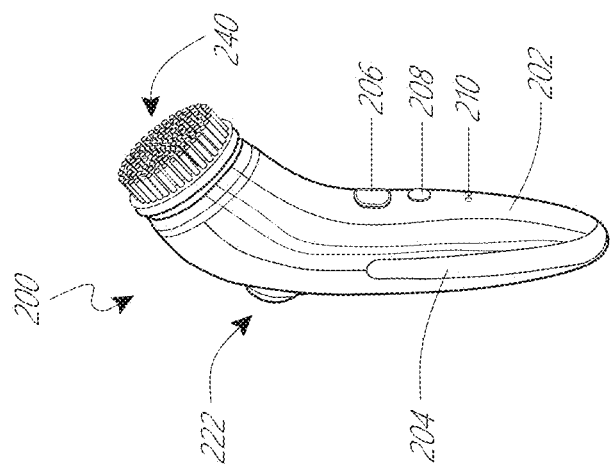
FIG. 2A shows a partial front view of an embodiment of a treatment device.

FIGS. 2A and 2B show an illustrative embodiment of a device 200 of the present disclosure. The device 200 can have a bent or dog-leg form. The device 200 can have a handle portion 202 that is sized to be gripped by the hand of a user. The handle portion 202 can include a gripping feature 204 that enhances the ability of a user to hold the handle portion 202. As shown in FIG. 2A, the gripping feature 204 can be a strip of material such as, for example, silicone that enhances a user's ability to grip the handle portion 202. In some arrangements, the gripping feature 204 enhances the ability of a user to grip the handle portion 202 when the handle portion is wet. The device 200 can include an indicator 206 that can indicate a status of the device, such as, for example the charge status of the device 200. The device 200 can include a controller 208 that allows a user to control the operation of the device 200. For example, the controller 208 can allow a user to modify the speed the device 200 rotates the attachment head 240. The device 200 can include a charging dock 210 that allows the device 200 to establish an electrical connection with a charging device.

As shown in FIGS. 2A and 2B, the treatment head 240 can be disposed on an end of the device 200. The treatment head 240 can be angled relative to the handle portion 202 by an angle of approximately 45°. The device 200 can include a fixed camera 222 that is disposed on the handle portion 202 in the vicinity of the bent region of the device 200. As shown in FIG. 2B, the fixed camera 222 can be disposed on a surface of the device 200 that faces away from treatment head 240.

Figure 3B:
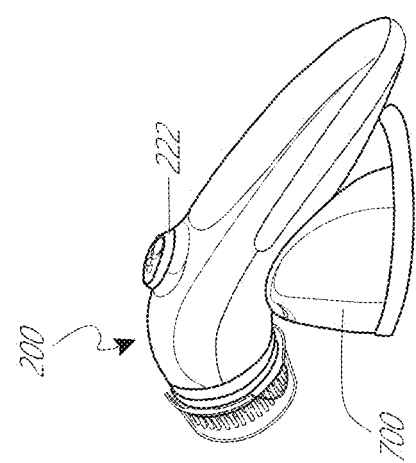
FIG. 3B shows a perspective view of the treatment device of FIG. 2A in the docking cradle of FIG. 3A.
Figure 3A:
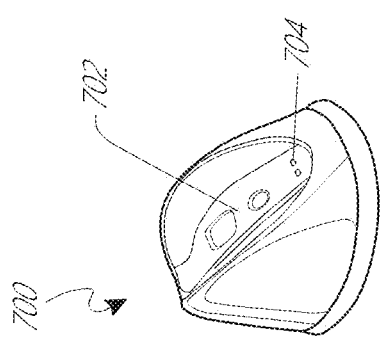
FIG. 3A shows a partial front view of an embodiment of a docking cradle.

FIG. 3A illustrates a docking cradle 700 for the device 200. The docking cradle 700 can include a recessed central portion 702 that can be sized to hold the device 200. The device 200 can rest in the docking cradle 700 in a substantially horizontal position, as shown in FIG. 3B. The docking cradle 700 can include a charging port 704 that aligns with the charging dock 210 (shown in FIG. 2A) of the device 200 when the device 200 is seated in the docking cradle 700. The charging port 704 and charging dock 210 can establish an electrical circuit when each is aligned with one another, thereby allowing the device 200 to be charged when the device 200 is seated in the docking cradle 700.

Figure 4B:
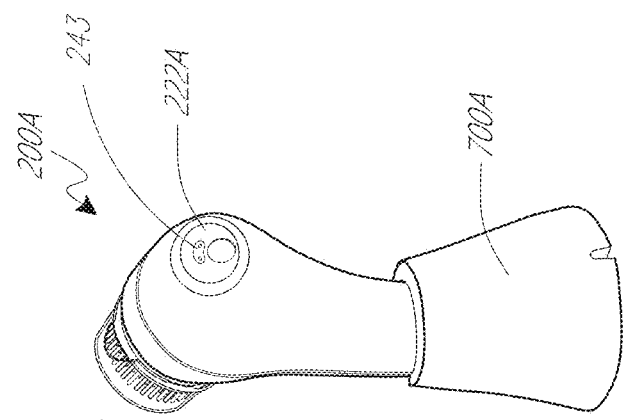
FIG. 4B shows a partial rear view of the treatment device and docking cradle of FIG. 4A.
Figure 4A:
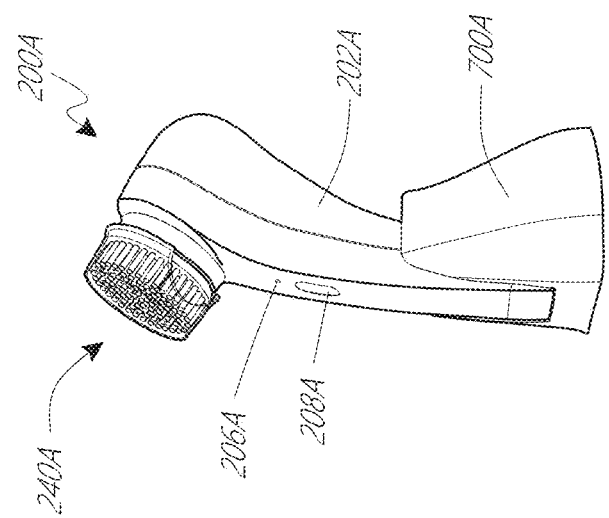
FIG. 4A shows a partial front view of an embodiment of a treatment device in a docking cradle.

FIGS. 4A and 4B illustrate an embodiment of a docking cradle 700A and a device 200A. The docking cradle 700A can be similar to the docking cradle 700 except as differently described. The device 200A can be similar to the device 200 except as differently described. The docking cradle 700A can be sized to hold the device 200A in a substantially vertical orientation, as illustrated in FIGS. 4A and 4B. The device 200A can include an indicator 206A and a controller 208A similar to the indicator 206 and the controller 208 as described with regard to the embodiment of the device 200 shown in FIGS. 3A and 3B. The device 200A can have a treatment head 240A that is substantially perpendicular to the handle portion 202A of the device 200A, as shown in FIG. 4A. The device 200A can include a fixed camera 222A that can be axially aligned with the treatment head 240A, as depicted in FIG. 4B. The fixed camera 222A can be disposed on the handle portion 202A on a side that is opposite of the treatment head 240A.

Figure 5B:
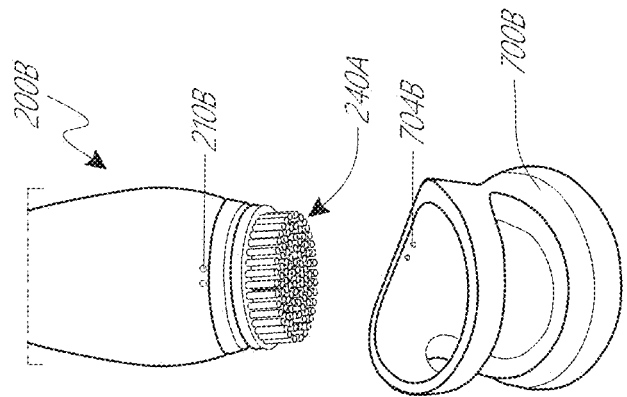
FIG. 5B shows the treatment device and docking cradle of FIG. 5A.
Figure 5A:
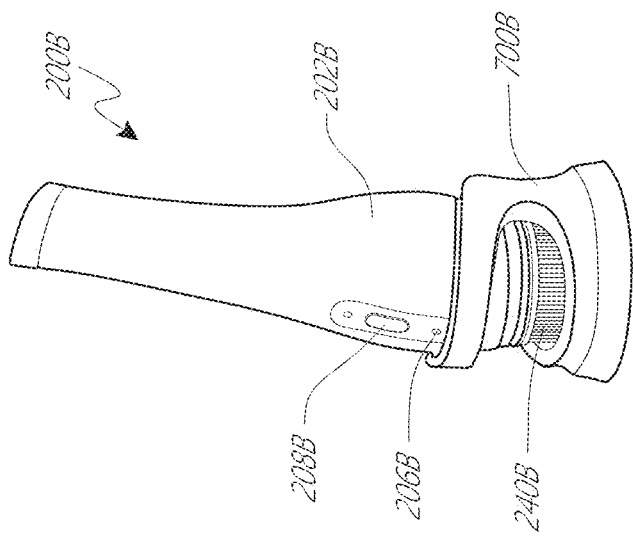
FIG. 5A shows a partial front view of an embodiment of a treatment device in a docking cradle.

FIGS. 5A and 5B illustrate an embodiment of a docking cradle 700B and a device 200B. The docking cradle 700B can be similar to the docking cradle 700A except as differently described. The device 200B can be similar to the device 200A except as differently described. The docking cradle 700B can be sized to hold the device 200B in a substantially vertical orientation, as illustrated in FIG. 5A. The device 200B can include an indicator 206B and a controller 208B similar to the indicator 206A and the controller 208A as described with regard to the embodiment of the device 200A shown in FIGS. 4A and 4B. The device 200B can have a treatment head 240B that is substantially axially aligned with the handle portion 202B of the device 200B, as shown in FIG. 5A. The device 200B can include a charging dock 210B that can align with a docking port 704B to allow the device 200B to charge when inserted into the docking cradle 700B, as described above.

Referring to FIG. 5C, the device 200B can allow different treatment heads 240 (e.g., a detachable camera 246B, a brush 242B) to be attached to the handle portion 202B of the device 200B. The detachable camera 246B can be similar to the detachable camera 246 described above, except as differently described below. The detachable camera 246B can be disposed on an end of the handle portion 202B. The detachable camera 246B can be axially aligned with a longitudinal axis of the handle portion 202B, as shown in FIG. 5C. The detachable camera 246B can seat within a platform 230 of the device 200B. The device 200B can include an interface 232 that establishes an electrical connection with the detachable camera 246B when the detachable camera 246 is seated in the platform 230. The interface 232 can be configured to transfer data from the detachable camera 246 and/or power to the detachable camera 246. The device 200B can include a drive shaft 234 that can drive a treatment head 240 (e.g., a brush 242B) when the accessory is seated on the drive shaft 234. For example, the drive shaft 234 can be adapted to rotate a brush 242B that is seated on the drive shaft 234.

Figure 5F:
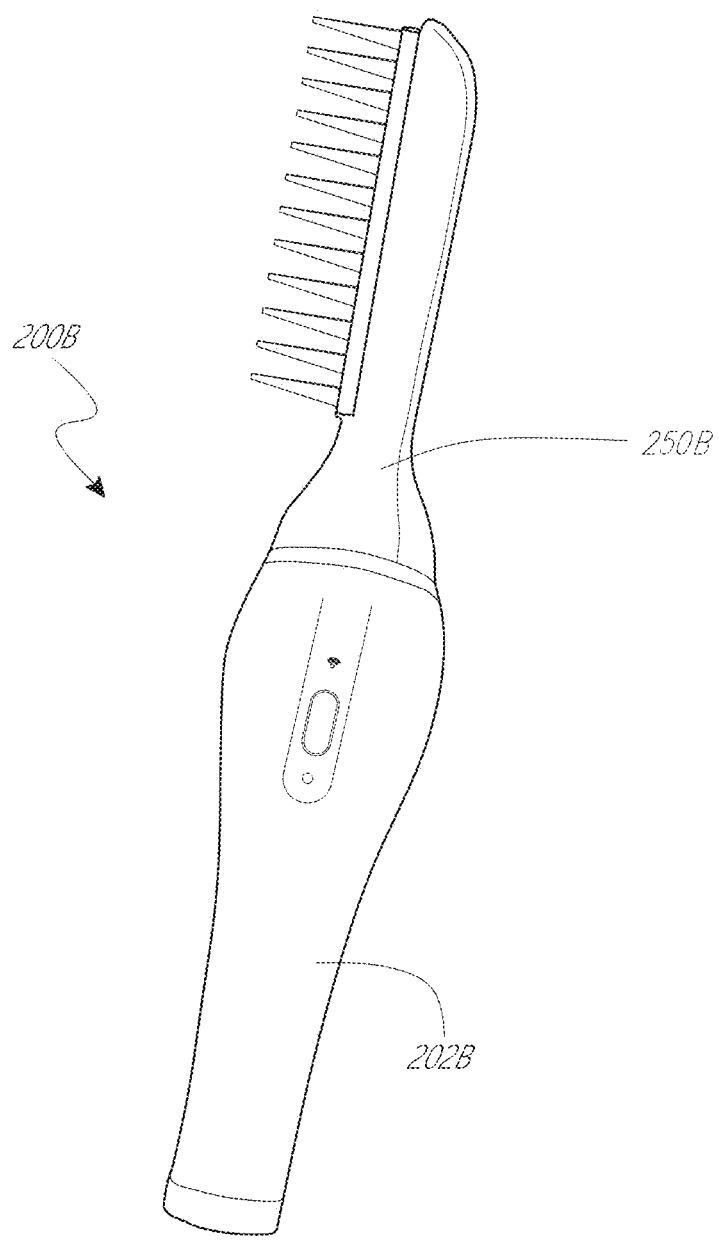
FIG. 5F shows the treatment device of FIG. 5C with a comb attached to the treatment device.

FIGS. 5D-5F show different treatment heads 240 (e.g., a detachable camera 246B, a treatment head 240B, a hair appliance 250) can be mounted onto the device 200B. FIG. 5D shows a device 200B with a detachable camera 246B mounted onto the device 200B. FIG. 5E shows a device 200B with a treatment head 240B mounted onto the device 200B. FIG. 5F shows a device 200B with a hair appliance 250B mounted onto the device 200B. As discussed, the treatment head 240B and the hair appliance 250B can each be configured to removably couple with a handle portion 202B that includes a fixed camera 222, 222A.

Figure 6:
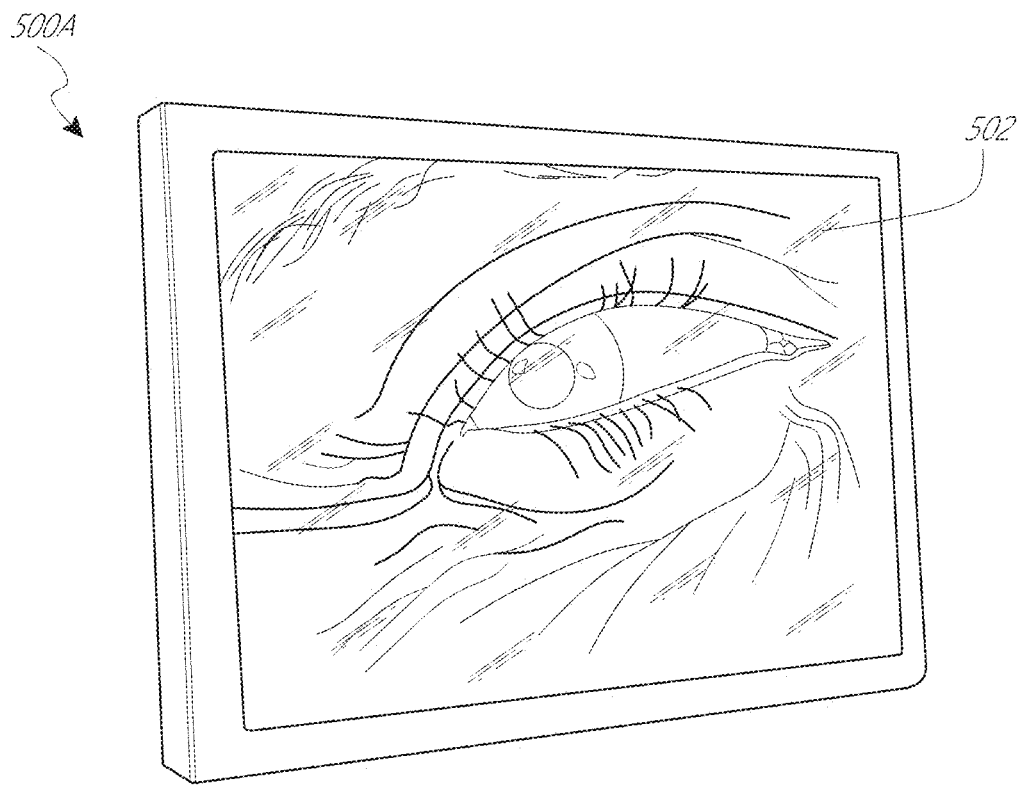
FIG. 6 shows an embodiment of a display which can be used in certain embodiments in combination with the treatment devices disclosed herein.

FIG. 6 shows an embodiment of a display 500A. The display 500A can be similar to the display 500 except as differently described. The display 500A can be a mini-monitor. The display 500A can come pre-loaded with the API 300 or configured to communicate with the API 300, as discussed above. The display 500 can have a screen 502 that displays an image, which in some embodiments may be presented within an interactive user interface that includes various user interface functionality described herein. The screen 502 can be a 5-inch screen. The screen 502 can allow a user to better see features of the skin, such as, for example pores or wrinkles. Accordingly, in certain embodiments the display 500A can be used and/or provided in combination with the devices 200, 200A, 200B described herein so as to provide a convenient standalone system in which the images captured from the devices 200, 200A, 200B can be displayed on the display 500A without the need for a separate display device.

Figure 7B:
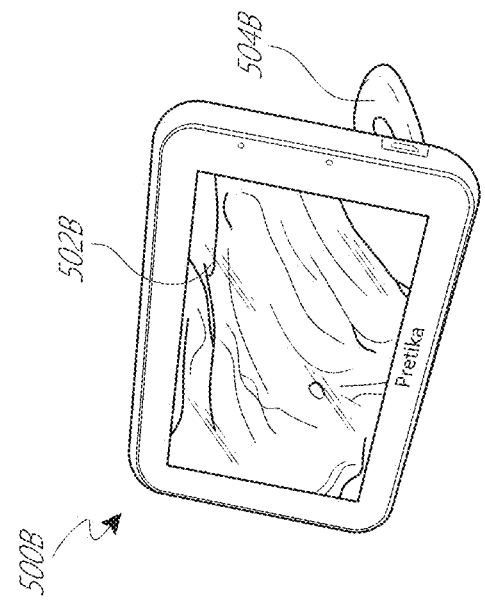
FIG. 7B shows the treatment device of FIG. 7A with the handle folded to support the display.
Figure 7A:
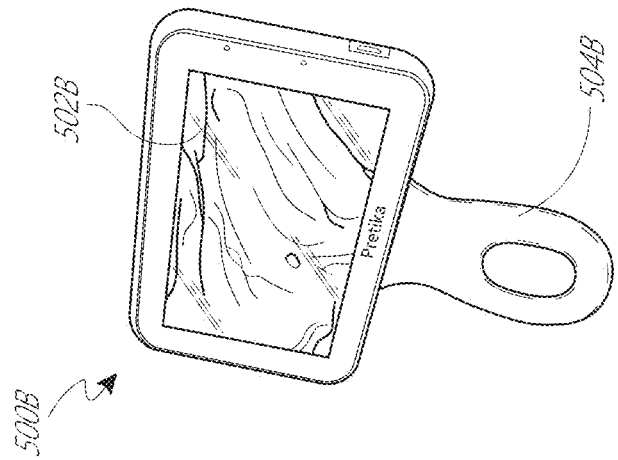
FIG. 7A shows an embodiment of a display having a handle.

FIGS. 7A and 7B show an embodiment of a display 500B having a foldable handle 504B. The display 500B can be similar to the display 500A except as differently described. The display 500B can be included with the device 200 so that a user need not have a mobile phone 400 or other home computing device (e.g., tablet, personal computer) in order to view images taken with the device 200 and/or to use the API 300 of the system 100. The foldable handle 504B can be moveable and can have an extended configuration (shown in FIG. 7A) and a folded configuration (shown in FIG. 7B). The foldable handle 504B can be arranged to pivot about the portion of the handle 504B that is attached at the back of the screen 502B. The foldable handle 504B can be rotated about the portion of the handle 504B that attaches at the back of the screen 502B, allowing the handle 504B to move between the extended and the folded configurations. In the extended configuration, the handle 504B can be substantially parallel with the screen 502B of the display 500B. When the handle 504B is in the extended configuration, a user can hold the display 500B as the user would hold a handheld mirror. In the folded configuration, the handle 504B can form an angle with the display 502B, allowing the handle 504B to serve as a base that supports the display 500B and holds the display 500B in a substantially upright orientation.

In the illustrated embodiment shown in FIG. 7B, the handle 504B forms an angle of about 60 degrees with the screen 502B, thereby holding the screen 502B about 30 degrees from vertical. In certain arrangements, the handle 504B forms an angle other than 60 degrees with the screen 502B. The handle 504B can be adapted to have a plurality of folded configurations. For example, the handle 504B can have a first folded configuration that holds the screen 502B about 10 degrees from vertical and a second folded configuration that holds the screen about 45 degrees from vertical. The handle 504B can have a folded configuration that holds the screen 502B from vertical by an angle of: 5 degrees, 10 degrees, 20 degrees, 30 degrees, 45 degrees, 60 degrees, 80 degrees, other values of degrees, and values therebetween.

In some arrangements, the foldable handle 504B can be reversibly attached to the display 500B. For example, the foldable handle 504B can be attached to a frame (not shown) that is sized to receive the display 500B, allowing a user to insert or remove the display 500B from the frame. In certain arrangements, the foldable handle 504B can be attached to a frame that is sized to receive a mobile phone 400, thereby allowing a user to attach the foldable handle 504B to the mobile phone 400 of the user.

Figure 8:
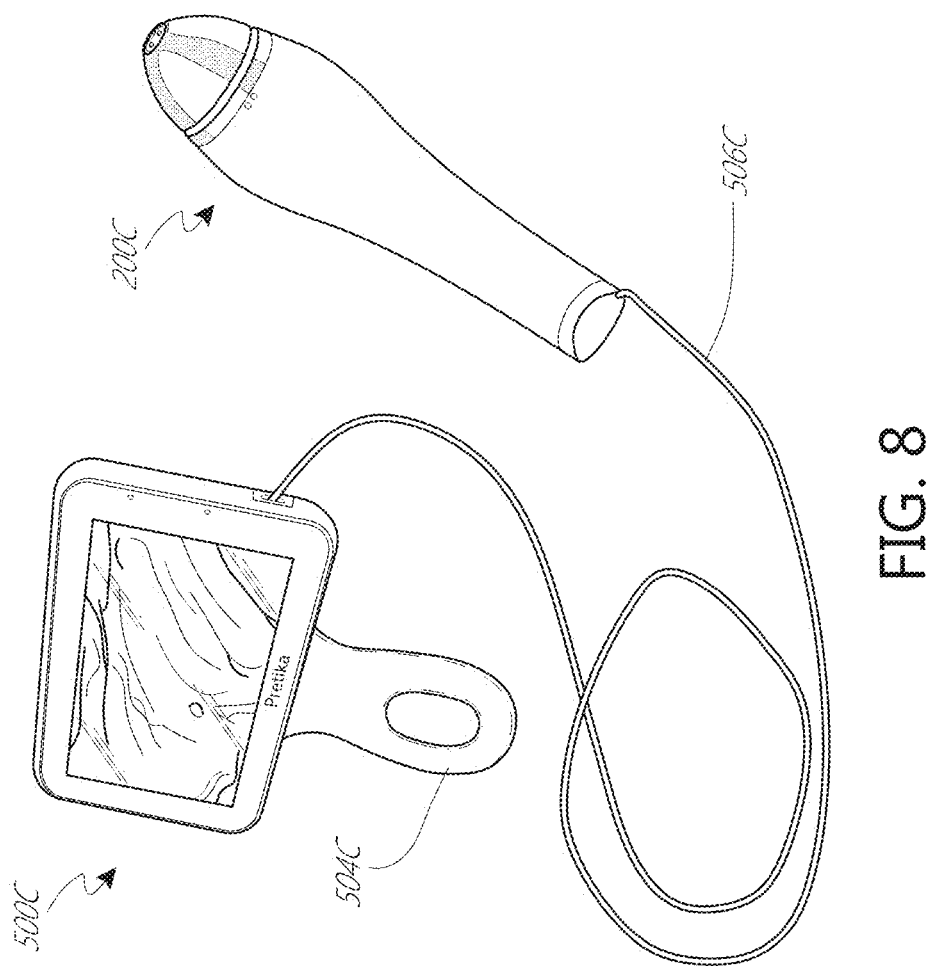
FIG. 8 shows the display of FIG. 7A in electrical communication with the treatment device through a wired connection.

FIG. 8 shows an embodiment of a display 500C having a foldable handle 504C. A cable 506C can be attached to the display 500C and to the device 200C. The cable 506C can be used to make a wired connection between the device 200C and the display 500C. The cable 506C can be used to transmit data between the device 200C and the display 500C. For example, the cable 506C can transmit to the display 500C image data that has been acquired by the device 200C, allowing an image captured by the device 200C to be displayed on the display 500C.

Figure 9:
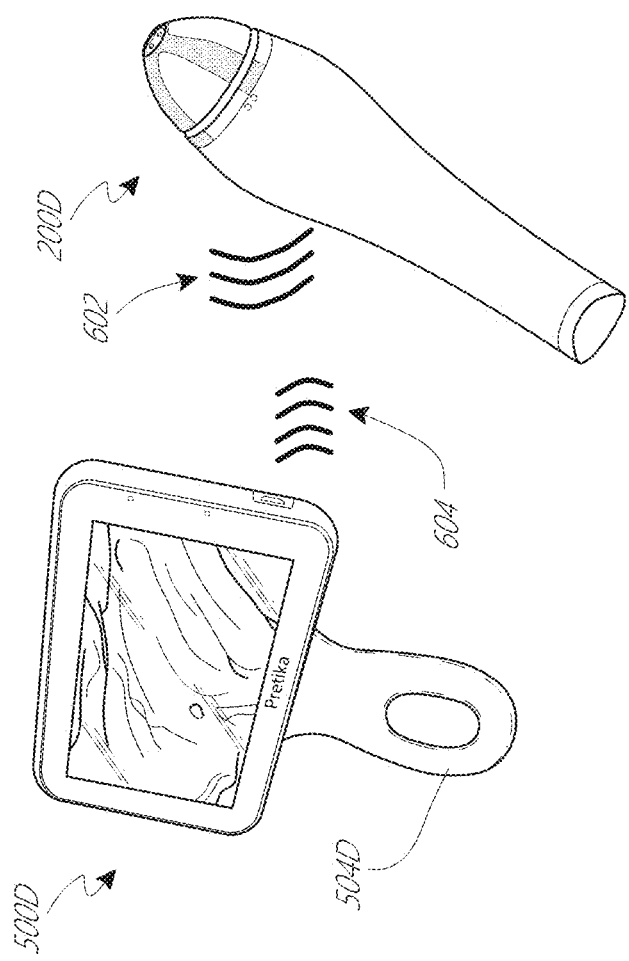
FIG. 9 shows the display of FIG. 7A in electrical communication with the treatment device through a wireless connection.

FIG. 9 shows a display 500D having a foldable handle 504D. The display 500D can be adapted to communicate with a device 200D through a wireless connection. The device 200D can transmit a device signal 602 that can be received by the display 500D. The display 500D can transmit a display signal 604 that can be received by the device 200D. The device signal 602 can include data (e.g., image data). The device signal 602 can include image data that can be displayed on the display 500D. For example, the device 200D can wirelessly transmit to the display 500D an image that was acquired by the device 200D, thereby allowing the display 500D to display the acquired image. The display signal 604 can include data (e.g., operational data). The display signal 604 can include data that modifies or controls operation of the device 200D. For example, the display signal 604 can include data that programs the device 200D to rotate a treatment head of the device 200D at a specific speed (e.g., rpm) for a specific amount of time.

Figure 10A:
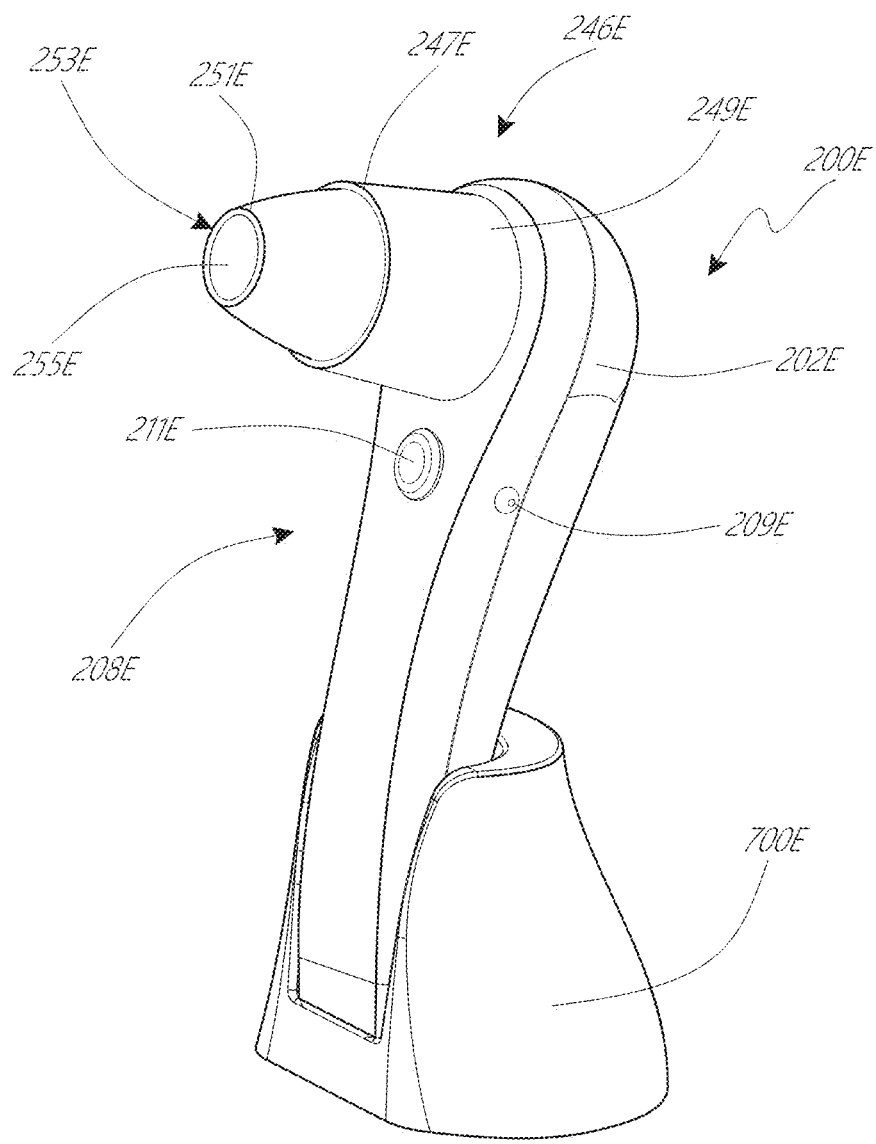
FIG. 10A shows a partial front view of an embodiment of a treatment device in a docking cradle.
Figure 10B:
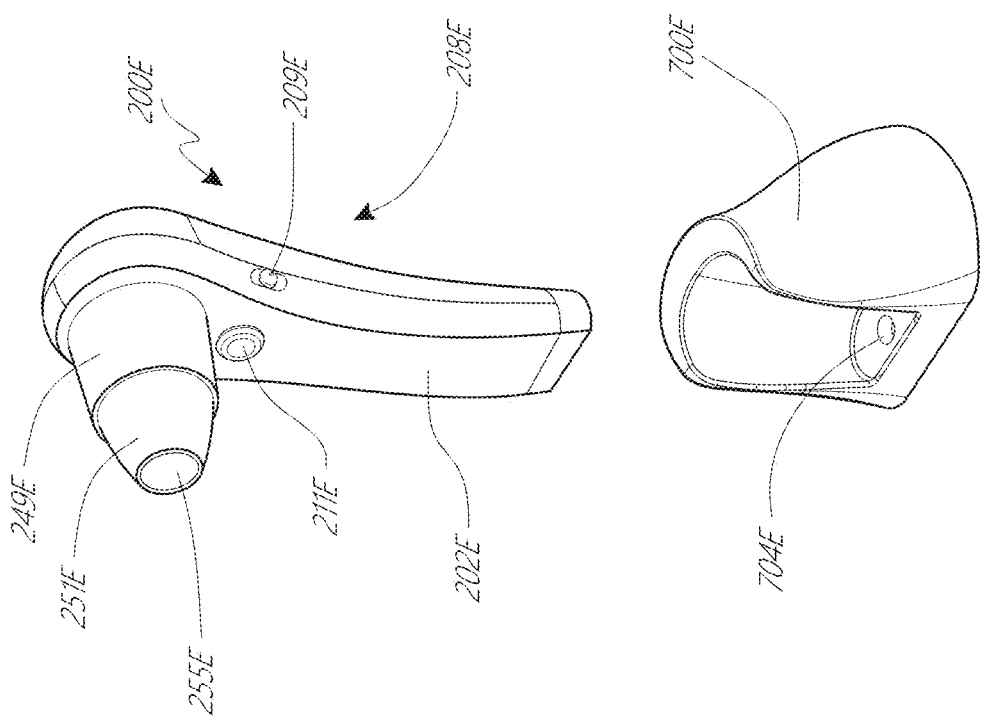
FIG. 10B shows the treatment device of FIG. 10A removed from the docking cradle.

FIGS. 10A and 10B illustrate an embodiment of a device 200E having a detachable camera 246E. The device 200E is shown seated in a docking cradle 700E in FIG. 10A. The device 200E is shown removed from the docking cradle 700E in FIG. 10B. The device 200E can be seated in the docking cradle 700E to charge the device 200E, as described previously. The device 200E can be similar to the device 200 except as differently described. The detachable camera 246E can be similar to the detachable camera 246 except as differently described. The docking cradle 700E can be similar to the docking cradle 700 except as differently described.

Referring to FIG. 10A, the detachable camera 246E can have a housing 247E. The housing 247E can have a base portion 249E. The base portion 249E can be adapted to attach to the handle portion 202E of the device 200. In the illustrated embodiment, the base portion 249E is substantially cylindrical. The housing 247E can have a tip portion 251E that is adjacent to the base portion 249E. In the illustrated embodiment, the tip portion 251E tapers away from the base portion 249E. The tip portion 251E can surround a central opening 253E of the housing 247E, as shown in FIG. 10A. In some arrangements, the central opening 253E is covered by a focusing lens 255E. In certain variants, the central opening 253E is not covered by a focusing lens 255E. As described in more detail below, the housing 247E can be shaped so that the detachable camera 246E is able to focus on a specific section of skin at a desired magnification. For example, the housing 247E can be arranged to provide the correct distance between the skin and a camera lens of the detachable camera 246E, allowing the detachable camera 246E to get the correct image of the skin.

The device 200E can have one or more controllers 208E that can be similar to the controller 208 except as differently described. In the illustrated embodiment, the device has a power controller 209E and a trigger controller 211E. The trigger controller 211E can activate the detachable camera 246E. For example, pressing the trigger controller 211E can activate the detachable camera 246E to take a picture. In certain arrangements, the trigger controller 211E can activate a treatment head 240 (shown in FIG. 1) that is attached to the device 200E. For example, pressing the trigger controller 211E can activate the treatment head 240 to rotate. The power controller 209E can override the trigger controller 211E. For example, the power controller 209E can be an ON/OFF switch. When the power controller is in the OFF position, the trigger controller 211E can be disabled such that pressing the trigger controller 211E does not activate a treatment head 240 or detachable camera 246E that is attached to the device 200E.

Figure 11:
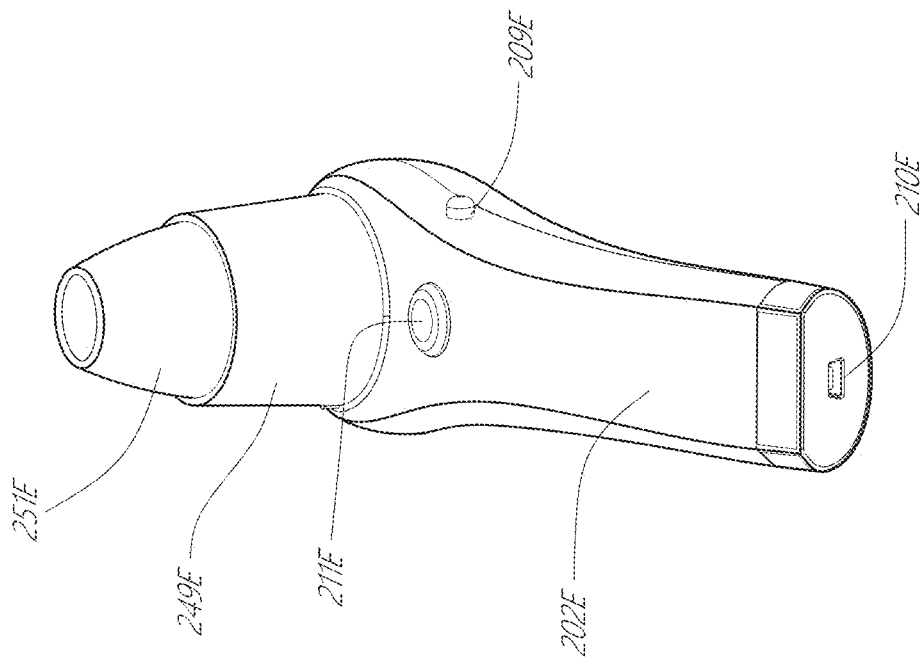
FIG. 11 shows a partial bottom view of the treatment device of FIG. 10A.

Referring to FIG. 10B and FIG. 11, the docking cradle 700E can have a charging port 704E that aligns with a charging dock 210E disposed on the device 200E when the device 200E is seated in the docking cradle 700E. As described previously with regard to FIGS. 2A-3B, the charging port 704E and the charging dock 210E can establish an electrical circuit when each is aligned with one another, thereby allowing the device 200E to be charged when the device 200E is seated in the docking cradle 700E.

Figure 12B:
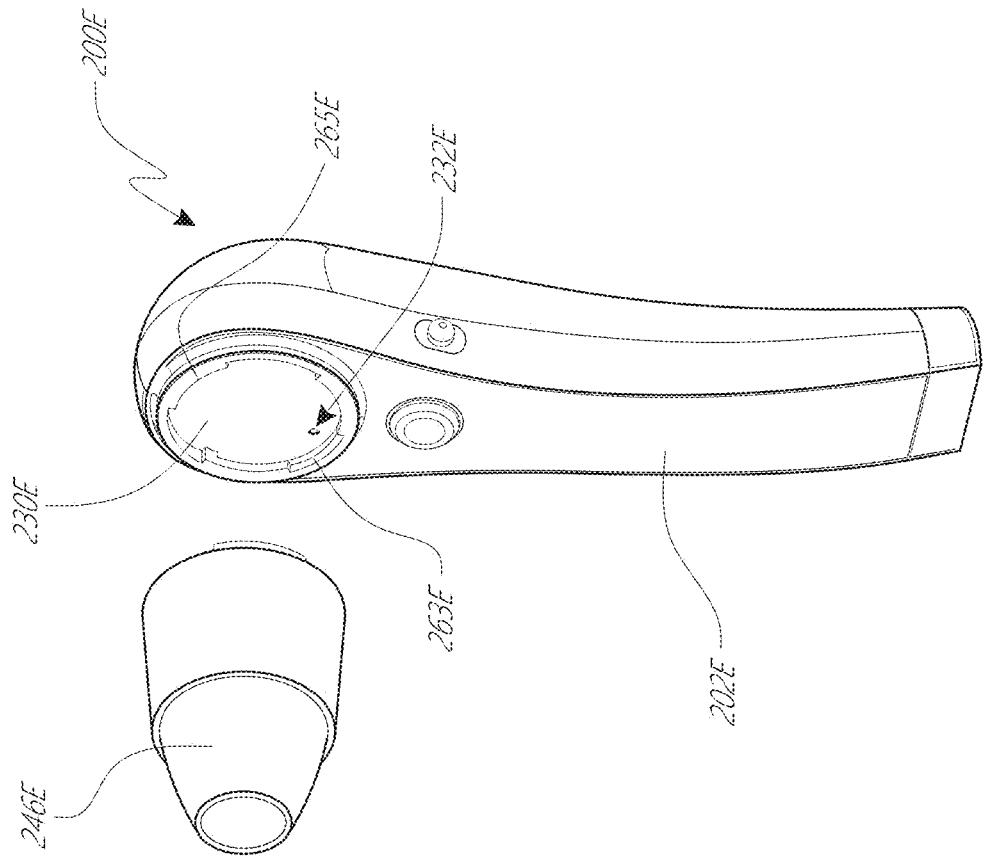
FIG. 12B shows the treatment device of FIG. 12B with the detachable camera removed from the handle portion.
Figure 12A:
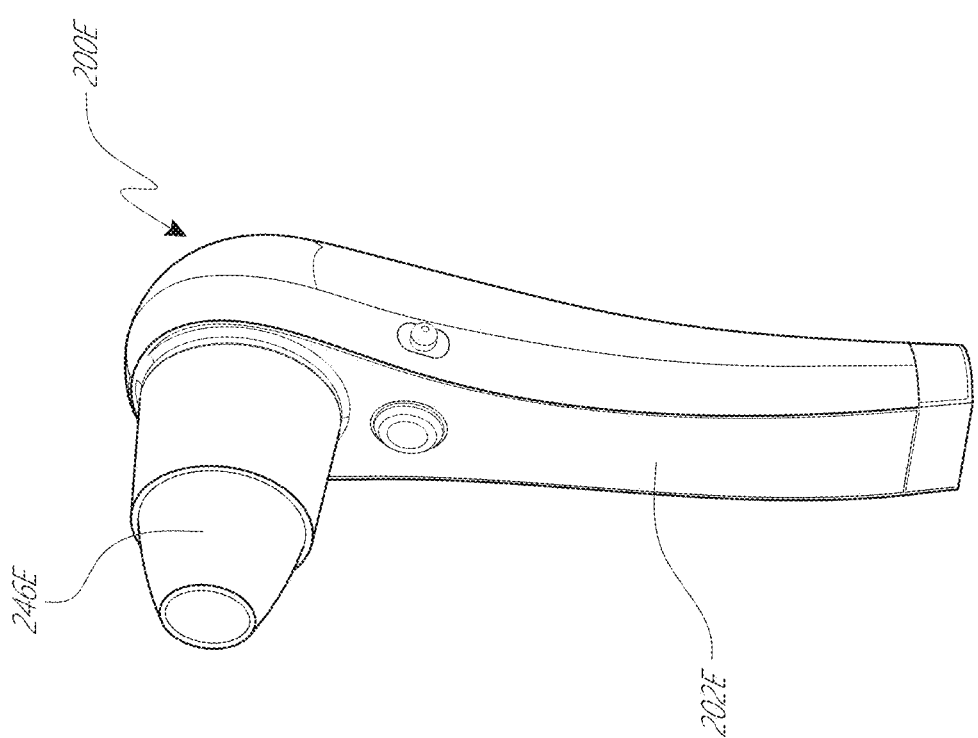
FIG. 12A shows a partial front view of the treatment device of FIG. 10A with the detachable camera attached to the handle portion.

FIGS. 12A and 12B illustrate that the detachable camera 246E can be reversibly attached to the platform 230E of the device 200E, as described with regard to FIGS. 5A-F. The detachable camera 246E is shown seated in the platform 230E in FIG. 12A. The detachable camera 246E is shown removed from the platform 230E in FIG. 12B.

FIGS. 13A-C illustrate different views of the detachable camera 246E. As shown in FIG. 13A, the detachable camera 246E can have a housing 247E that has a substantially cylindrical base portion 249E that is joined to a tapered tip portion 251E. FIG. 13B is a bottom view of the detachable camera 246E, illustrating that the base portion 249E can include features to allow the detachable camera 246E to attach to the platform 230E (shown in FIG. 12B) of the handle portion 202E. In the illustrated embodiment, the base portion 249E has a collar 257E that is shaped to seat into the platform 230E in a first orientation and then be locked to the platform 230E when the detachable camera 246E is rotated to a second orientation. For example, referring to FIGS. 12B and 13B, the detachable camera 246E can include one or more tabs 261E that can be inserted into a corresponding recess 263E of the platform 230E. The detachable camera 246E can then be rotated to bring the tab 261E underneath a flange 265E of the platform 230E, thereby locking the detachable camera 246E onto the handle portion 202E. The platform 230E can have an interface 232E that aligns with a corresponding interface 267E on the collar 257E when the detachable camera 246E is locked onto the handle portion 202E.

FIG. 13C is a cross-sectional view of the detachable camera 246E. In the illustrated embodiment, the detachable camera 246E is hollow with the base and tip portions 249E, 251E circumferentially surrounding a longitudinal axis of the detachable camera 246E. The detachable camera 246E can include a light source 269E that is circumferentially surrounded by the housing 247E. The light source 269E can illuminate the skin that covers the central opening 253E of the detachable camera 246E when the detachable camera 246E is in contact with the skin. The light source 269E can be configured to emit different light at different wavelengths and intensities. For example, the light source 269E can emit a first combination of light wavelengths and intensities that foster the imaging of wrinkles. The light source 269E can emit a second combination of light wavelengths and intensities that foster the imaging of pores. The second combination of light wavelengths and intensities can be different from the first combination of light wavelengths and intensities. The device 200E can allow a user to select the wavelengths and intensities of light that are emitted by the light source 269E. The light source can be an LED. The light source can be a light source other than an LED. The LED lights can be configured to illuminate the skin for consistent images. The lights can be in a cross-polarized configuration with the camera. The cross-polarization of the lights with the camera can allow the camera to see slightly beneath the surface of the skin.

The detachable camera can include a camera lens 271E. In the illustrated embodiment, the camera lens 271E is disposed near the collar 257E. The base and tip portions 249E, 251E of the housing 247E can be sized so that camera lens 271E is the correct distance from the skin when the detachable camera 246E is in contact with the skin. In other words, the housing 247E can be sized so that the distance between the camera lens 271E and the end of tip portion 249E that surrounds the central opening 253 is the correct focal length to produce a sharp image of the skin at the desired magnification.

In some embodiments, the detachable camera 246E can include a focusing lens 255E. In the illustrated embodiment, the focusing lens 255E is disposed at the narrow end of the tapered tip portion 251E. The focusing lens 255E can be adapted to focus light on the camera lens 269E to produce a sharp image of the skin at the desired magnification.

Figure 14:
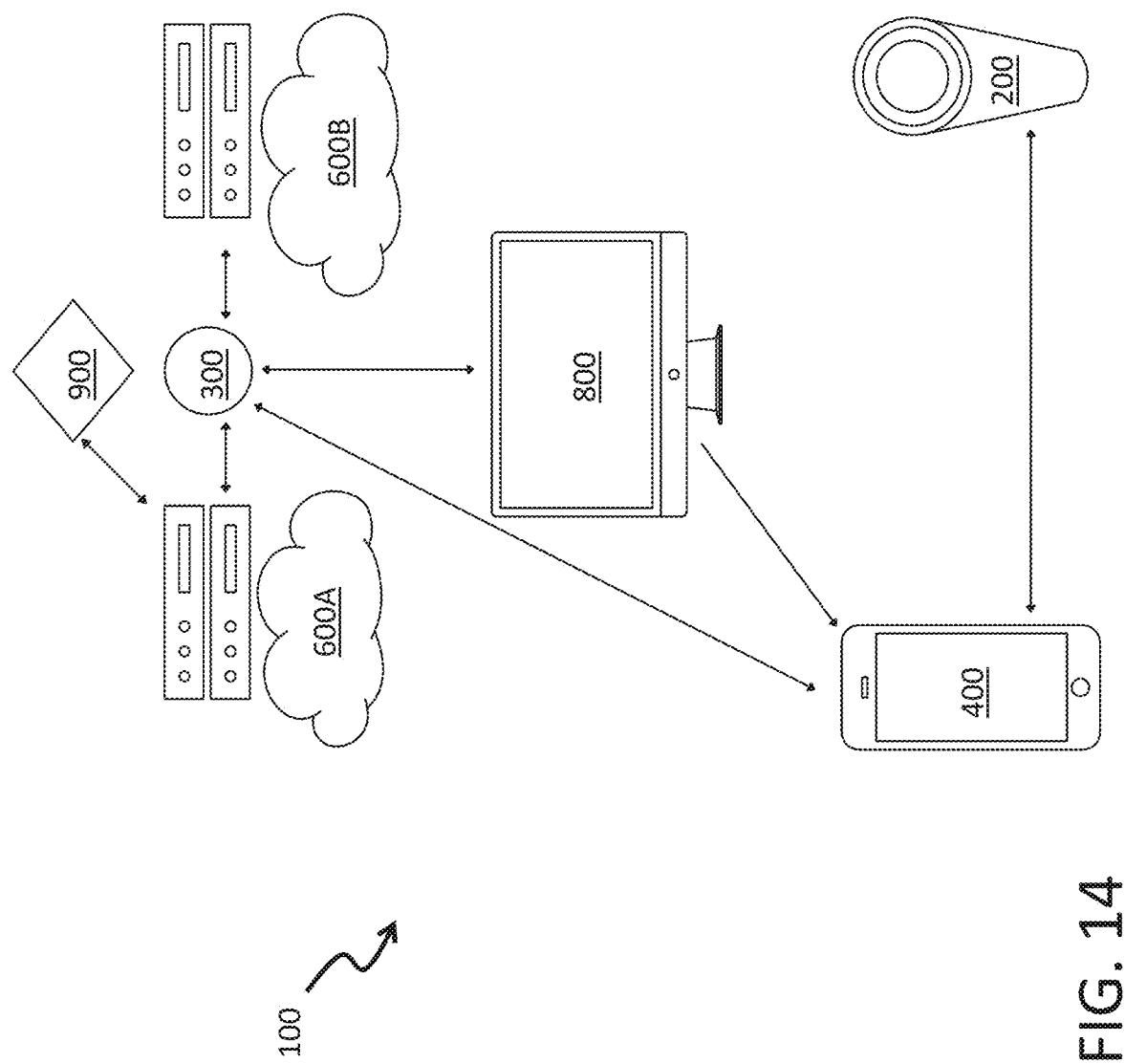
FIG. 14 shows an embodiment of a content management system of the personal care system.

FIG. 14 illustrates that the system 100 can communicate with a content management system (CMS) 800, which may implement a web application or service that is remotely accessible by the mobile device 400 and/or device 200, such as via the API 300. The CMS can allow the system 100 to download or display educational information, provide instructions for use manuals, provide company brand information, display purchasing information with links to online and retail sellers, or other content via the API 300. The CMS can be configured to recommend products to the user, modify static content on the mobile app, provide a portal to review communications with the API 300 or other component of the system 100, and provide analytics. The system 100 can communicate with the CMS 800 to input educational or historical data and images to allow the user to make notes comparing results of the system 100 with topical and other treatments used in conjunction with the system 100. As discussed the mobile application can be supported on IOS, Android and/or other device operating system, and can pull in operating software data using the API 300.

The CMS 800 can keep daily, weekly, monthly, or annually grouped historical data for the user. The CMS 800 can implement functionality to virtually measure, estimate or calculate wrinkle depth comparison of the before and after photos from each treatment or use of the device 200, such as via automated comparisons of the images (which may include applying transformations to the image data, generating features from the image data for input to a machine learning model, and/or other methods). The before and after photo images of the system 100 can show the condition (e.g., dry, flaking skin) of the epidermal layer or wrinkle and fine lines. The CMS 800 can note the day and time of each treatment or use of the device 200. Images taken from the device 200 can be uploaded or otherwise transferred to skin care professionals. The CMS 800 can allow a user to communicate with the device company by email or text messaging. The CMS 800 can allow the device to display an interactive menu that allows the mobile application to recommend (and optionally offer for purchase) other company products directly to the user (where the recommended products may be based on the results of the automated image analysis) and allow the user to directly communicate with the company. The CMS 800 can provide custom skin care routines, how to use tips, user manual information, or treatment recommendations. The CMS 800 or API 300 can allow the user to sign up for exclusive offers (e.g., discounts off of next orders, early notice about new products, skincare tips). The CMS 800 can provide links to connect with other forms of social media (e.g., Facebook, Twitter, Instagram, and pinterest). The CMS 800 can allow the system 100 to be configured for a single user setup or a multiple user set up.

The system 100 (e.g. the CMS 800 or the API 300) may include or communicate with artificial intelligence (AI) or machine learning components. The system 100 can provide personalized, AI-based integrative solutions. The AI-based solutions can be based on images of the user's skin or hair or other data associated with the user. The system 100 can provide AI beauty and lifestyle skin-data-based integrative personalized solutions to home beauty care users based on interactive AI and data intelligence technology within the API 300 or CMS 800. For example, in one embodiment, one or more servers 600 may implement one or more machine learning models that have been trained to identify various skin or hair information described herein (such as wrinkle depth, etc.) based on one or more images (and/or associated metadata) provided to the model as input. In some embodiments, an operator or administrator of a server 600 or the API described herein may provide one or more machine learning models with labeled training data in order to train the model(s). The one or more machine learning models may implement any of various classification algorithms or regression algorithms known in the art in order to generate output of the model(s). As one example, training images depicting human faces may be labeled with the locations within the image and associated depths of skin wrinkles within the images, which may be provided to a machine learning model in order to train the model to identify skin wrinkles (such as via one or more classification algorithms or model types) and predict a numeric depth of each identified wrinkle (such as via one or more regression algorithms or model types). The trained model(s) may be periodically updated or retrained based on additional images, sensor data and/or other data received from use of the device 200 by users. The trained models may be operated remotely from the use location of the device 200 (such as by the model being implemented at a server that is provided input data via the API described herein), or the trained model may be integrated within a mobile application or otherwise provided for local execution at the mobile device 400 or device 200.

The camera 222, 246 can include one or more sensors 243 (FIGS. 4B and 5C). The sensors 243 can be configured to provide data on skin or hair condition. For example, the sensor 243 can be configured to measure or analyze one or more of the following: moisture, pores, sebum, elasticity, fine lines, and/or wrinkles. The sensor 243 can include a capacitive sensor, an optical sensor (e.g., a photodiode), and/or an elasticity oscillating probe sensor. The sensor 243 can be configured to acquire data on skin or hair condition simultaneously or in conjunction with the camera 222, 246 taking images of the skin or hair. In some arrangements, the sensor 243 can acquire data on the condition of the skin or hair independent of the camera 222, 246 taking an image of the skin or hair. The system 100 can be configured to associate or link an image from the camera 222, 246 with the corresponding data from the sensor 243. In some variants, the sensors 243 can surround the camera lens. The system 100 can be configured to analyze the user's face with AI and the image and sensor data from the camera 222, 246. The system 100 can allow a user to track skin progress. The system 100 can give information about the health and actual needs of the user's skin. The camera 222, 246 can show a digital image of wrinkles of a user's skin. The API 300 or CMS 800 can analyze the number of wrinkles, the depth of the wrinkles, the length of the wrinkles, and how much the wrinkles branch off. The API 300 can map out skin pores in a similar way.

In some embodiments, input images, associated metadata, sensor data, and/or other input features captured from the device 200 may be provided to multiple machine learning models, such as convolutional neural networks or other deep neural networks, which are each trained to identify and assess different aspects of the images or other input features. For example, one or more of the machine learning models or individual layers within a model may be trained to identify and assess (such as assessing a quality, depth or extent of damage, depending on the output type of a given model) one or more of: moisture, pores, sebum, elasticity, fine lines and/or wrinkles. Some models may be trained to receive images or related image features as input, while other models may additionally or alternatively receive input data generated from one or more sensors of the device other than a camera, such as a sensor capacitive sensor, photodiode optical sensor, elasticity oscillating probe sensor and/or others. The weights assigned to each of the various input features (such as features captured by or derived from the different sensors) when predicting a given output variable may be learned in a training process. It will be appreciated that any of various machine learning model types or associated algorithms may be employed, such as any of various supervised learning models including but not limited to a Naive Bayes classifier, a linear regression model, Support Vector Machines, neural networks in various forms, a k-NN algorithm, etc.

In addition to being provided for display to a user, output of one or more machine learning models described above may be provided as input to further models, algorithms or modules. For example, a module may be configured to recommend skincare products and/or other home beauty care services or treatments to a user based on the above model output. Another module may be configured to track improvement or other changes to one or more conditions or health factors of a user's skin over time, such as tracking progress in the machine learning model's assessment of a user's wrinkle depth across images taken over a given time period (e.g., over the length of time that the user uses the device 200). Additional uses of the models' output may include recommending device settings or treatment regimens for the user's use of the device 200.

The system 100 can include a computer chip or component(s) of a computer-based control system that stores a computer program. In some embodiments, the component(s) of a computer-based control system can store computer program instructions, for example, within a non-transitory computer-readable storage medium such as a persistent magnetic storage drive, solid state drive, etc. The execution of those instructions may control the entire system 100 or sub-system(s) thereof. For example, when executed by a processor of the system 100, the instructions may cause the components of the system 100 to communicate data between one another. The functions of the CMS 800 or other components of the system 100 described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The chip or computer-based control system can include a wireless receiver or other similar component adapted for receiving commands sent from the API 300 or from the network to which the system 100 is connected. The computer chip can listen for commands sent from the API 300 over the network to which the system 100 is connected. The computer chip can include a transmitter for transmitting information to the API 300 or to the network on which the system 100 is connected. The computer chip can post status and data about its current functioning state to the API 300 or to the network on which the system 100 is connected. The system 100 can include a wireless transmitter and receiver that allows the system 100 to communicate with a WiFi modem. The system 100 can communicate with a mobile device 400 directly or through an intermediary WiFi modem. The WiFi modem can allow the system 100 to transmit and receive signals over the internet with a cloud server 600A, 600B. The cloud server 600A, 600B can act as an intermediary between the system 100 and the CMS 800 that is used for maintaining the API 300.

The system 100 can include a printed circuit board assembly (PCBA). The PCBA can include a printed circuit board (PCB). The PCB can include a main processor, a Wi-Fi antenna (e.g., IPEX antenna), a power management unit (PMU), a power control button, an LED indicator light, resistance and capacitive components. The PCBA can be in communication with the camera 222, 246, 222F (discussed below) and the one or more sensors 243, 243F (discussed below). The PCBA can communicate with a lens module with sensor. The camera 222, 246, 222F can be a two mega pixel 1920×1080 camera. The camera 222, 246, 222F can communicate with the PCBA through a cable connected to the main board of the PCBA. The system 100 can include a power cord from the PCBA to an internal battery. The internal battery can be rechargeable. The system 100 can be configured to be powered through direct connection to a wall power outlet. The system 100 can be configured to recharge the internal battery through direct connection to a wall power outlet. As discussed, the system 100 can include a USB connector port on the device 200. The USB port can enable the direct transfer of measurement data onto a PC or notebook. The system 100 can include software that allows management of the results and storage of data (e.g., image archiving) on a screen of a computer or mobile device, as described herein.

The CMS web application 800 can be maintained by the company that manufactures or sells the system 100. The mobile application of the system 100 can display an interactive menu that allows the mobile application to sell other company products directly to the user and allow the user to directly communicate with the company. The user can download the mobile application from the website of the company that manufactures or sells the system 100. The application can allow the user to set skin goals, sync routines, track progress, and earn rewards. In some embodiments, the user selects the device 200 by model number, name, or picture image when the application is opened. The CMS web application 800 can control the images taken with educational information and manage the ecommerce section of the mobile application. The CMS web application 800 can save data to a database of the API 300. The mobile application of the system 100 can retrieve the data saved by the CMS 800 to the database of the API 300. The mobile application of the system 100 operating on a mobile device 400 can keep track of the daily, weekly, monthly, or annually use of the system 100.

With continued reference to FIG. 14, the system 100 can include one more machine learning software components or modules 900. The component(s) 900 can communicate with a computer chip or component(s) of a computer-based control system of the system 100. The computer chip can communicate with a first server 600A or a second server 600B. The first server 600A can include applications or software that enable the calculations for measuring and monitoring skin features (e.g., wrinkle depth) or other analytics, as discussed herein. The second server 600B can include applications or software that enables the storage or archiving of user images and other data. The CMS web application 800 can be accessed on a mobile device 400 using a cloud-based graphical user interface (GUI) associated with the CMS 800 and various features of the CMS 800, such as via either a browser (such as a web browser) or a dedicated application installed on the mobile device 400.

Figure 15A:
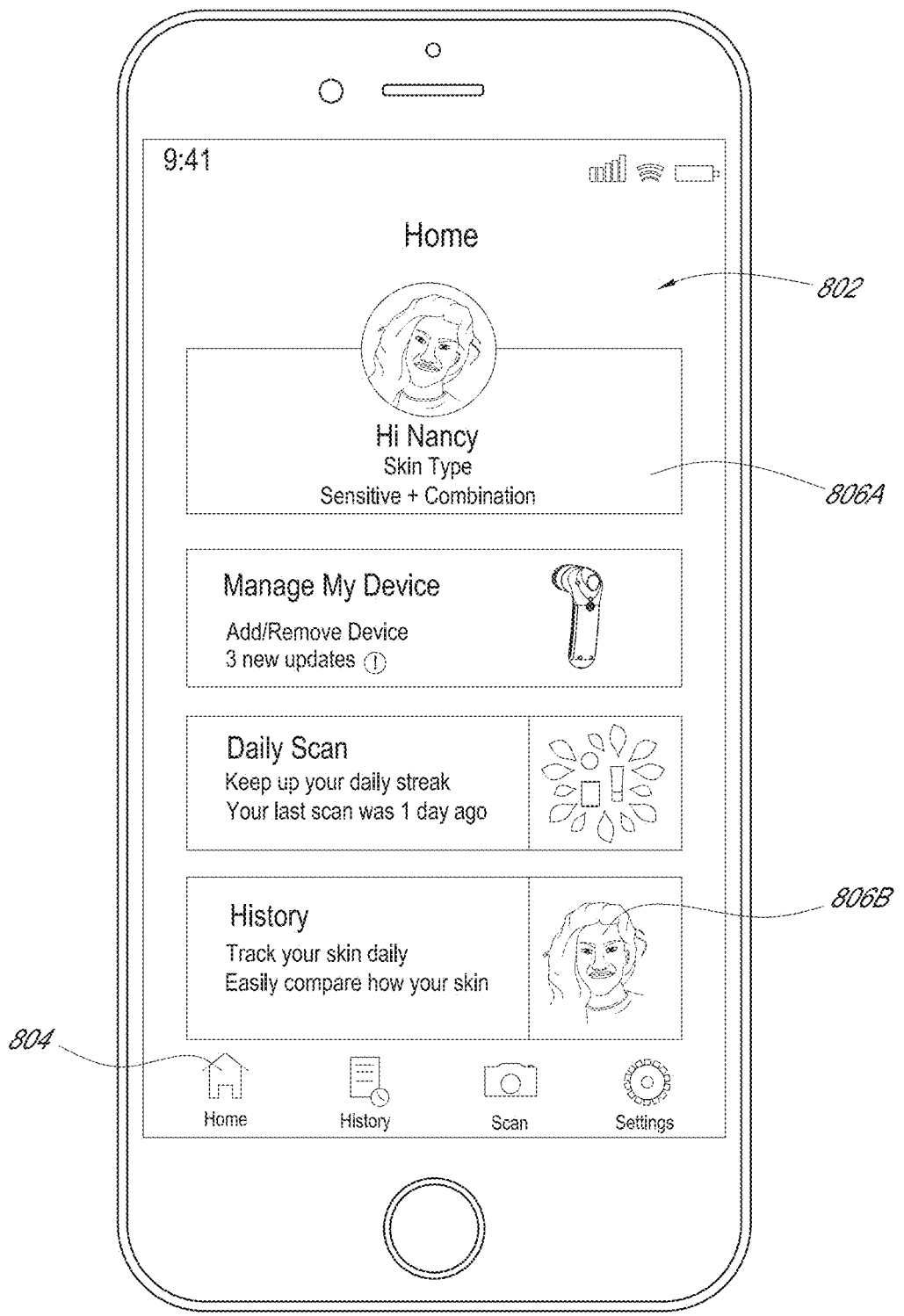
FIG. 15A shows an embodiment of a graphical user interface of the personal care system.
Figure 15C:
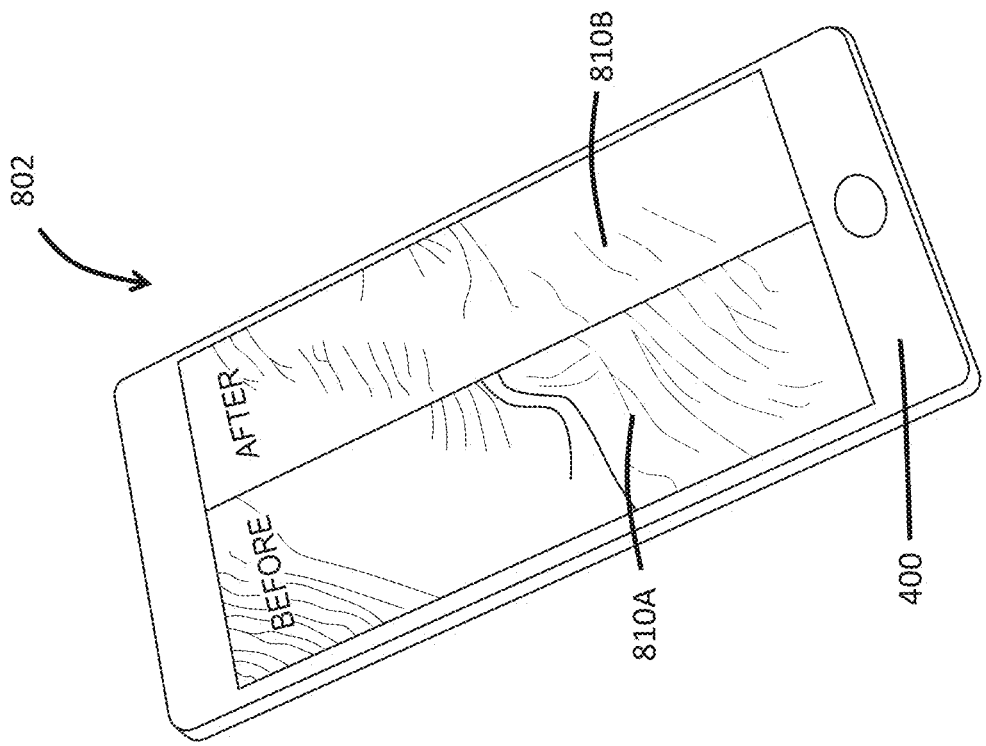
FIG. 15C shows an embodiment of a graphical user interface of the personal care system.
Figure 15B:
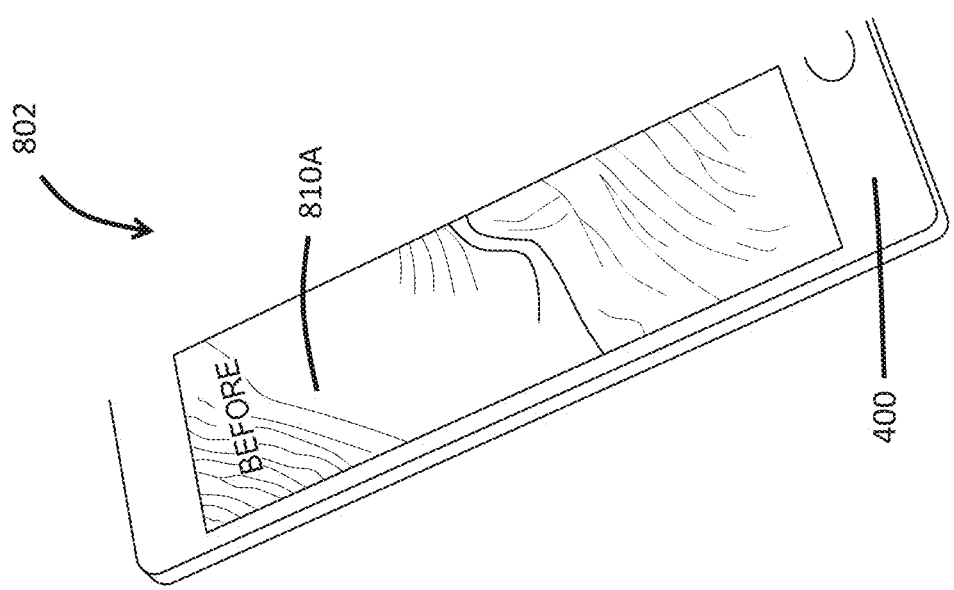
FIG. 15B shows an embodiment of a graphical user interface of the personal care system.

FIGS. 15A-15C illustrate an embodiment of a GUI 802 which may be generated by the CMS web application 800 and/or by the mobile device, and which allows a user to interact with the CMS 800. In the illustrated embodiment, the GUI 802 is displayed on a mobile device 400. The GUI 802 can include a menu icon 804 that allows the user to access different features of the CMS 800 or mobile app. The GUI 802 can include one or more display windows 806A, 806B. The GUI 802 can have a display window 806A that allows the user to access information such as: company contact info or other information about the company; user tips (e.g., skin care routines, how to use the device 200, user manuals, treatment recommendations). FIG. 15B shows that the GUI 802 can include a first image field 810A. The first image field 810 can show a real-time image from the camera of the device 200. The user can hold the device 200 over the area of the skin to be treated and view the real-time image of the skin in the first image field 810A. The user can scroll or move the device 200 until a desired portion of the skin is displayed in the first image field 810A, at which time the user can press a shutter icon on the GUI 802 to take a picture of the skin. After the picture is taken of the skin, the first image field 810A can display this image as a before picture of the skin to be treated. FIG. 15C illustrates that the GUI 802 can include a second image field 810B. The second image field 810B can display the skin after the skin was treated. The second image field 810B can be a real-time image that is updated as the user moves or scrolls the device 200 over the skin. In some embodiments, the user scrolls the device 200 over the skin until the second image field 810B displays the same region of skin as shown in the first image field 810A (the before treatment image). After the device 200 is properly positioned on the skin, the user can press an icon on the GUI 802 to capture a second image (the after treatment image) in the second image field 810B. The images captured in the first and second image fields 810A, 810B can then be transferred to the CMS 800 or API 300 for further processing, as described herein.

Figure 16B:
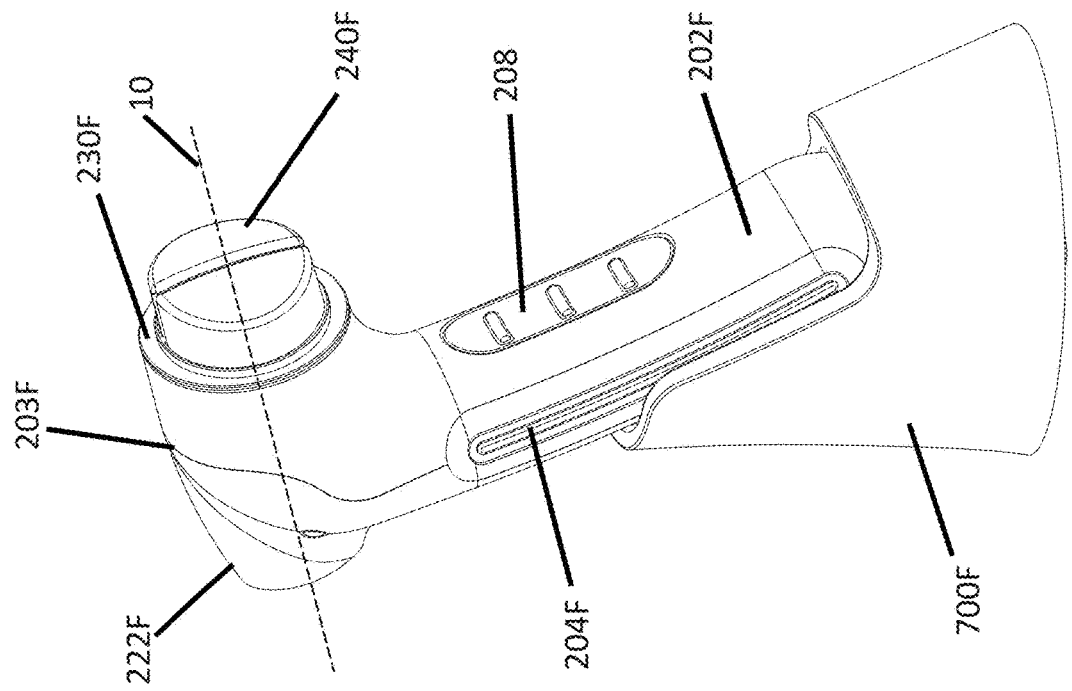
FIG. 16B shows a partial front view of the treatment device of FIG. 16A.
Figure 16A:
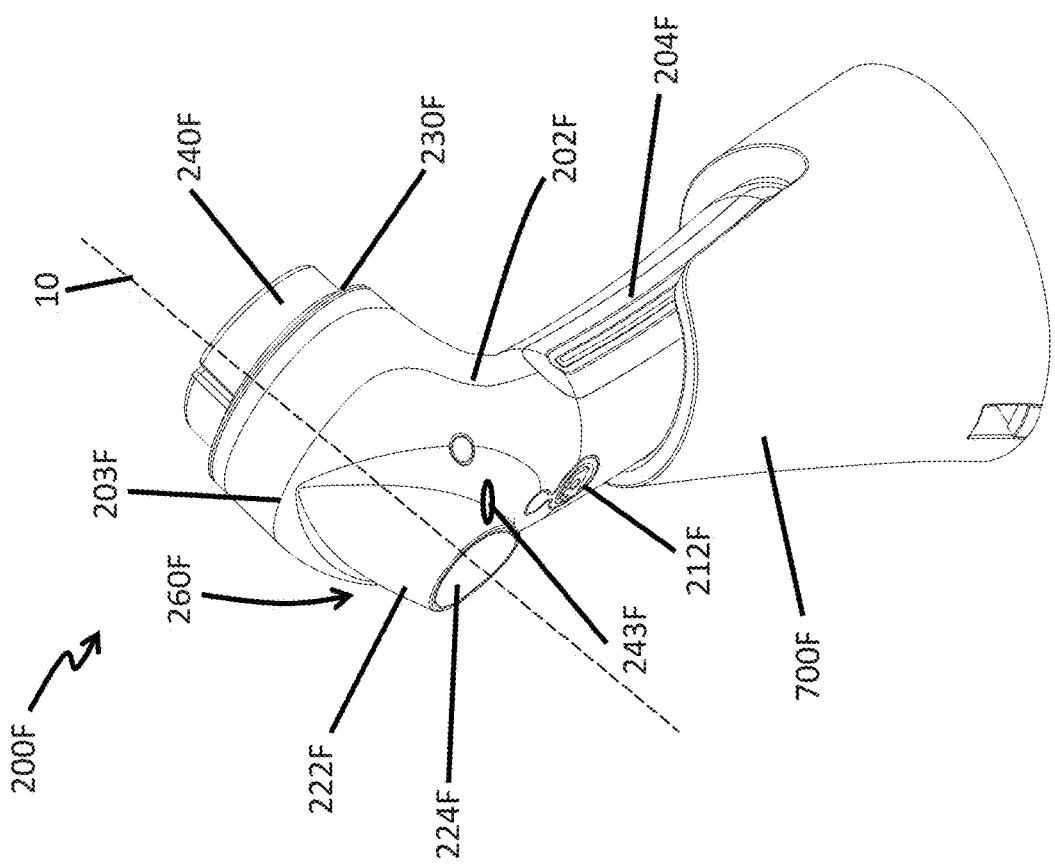
FIG. 16A shows a partial rear view of a treatment device according to some aspects of the present disclosure.

FIGS. 16A and 16B show a treatment device 200F that is similar to the treatment device 200 except as differently described. In certain embodiments, the treatment device 200F can be used in combination with the features described above including those discussed in context with the treatment devices 200, 200A, 200B, 200C, 200D, 200E described above including, for example, the system 100, the CMS web application 800, the API 300, the mobile device 400, CMS 800, machine learning components or modules 900, display, and/or docking cradle.

As discussed, the device 200F can have a handle portion 202F that is sized to be gripped by the hand of a user at grip portion. The device 200F can have a head portion 203F that is disposed at an end of the handle portion 202F. The device 200F can include a treatment head 240F and a camera 222F.

In the illustrated embodiment, the camera 222F is fixed to the treatment head 240F and referred to herein as a fixed camera but in modified arrangements the camera 222F could be removable. The treatment head 240F and the fixed camera 222F can be disposed on the head portion 203F of the device 200F, as shown. The fixed camera 222F can be configured as a lens module 260F that allows the fixed camera 222F to image the skin with or without the device 200F making contact with the skin, as described herein. The device 200F can be docked in a docking cradle 700F to charge a battery that is housed in the handle portion 202F, thereby allowing the device 200F to be used in a cordless mode of operation. In some variants, the device 200F can be powered by plugging the device 200F into a wall electrical outlet such that the device 200F can be used in a corded mode of operation.

Figure 17:
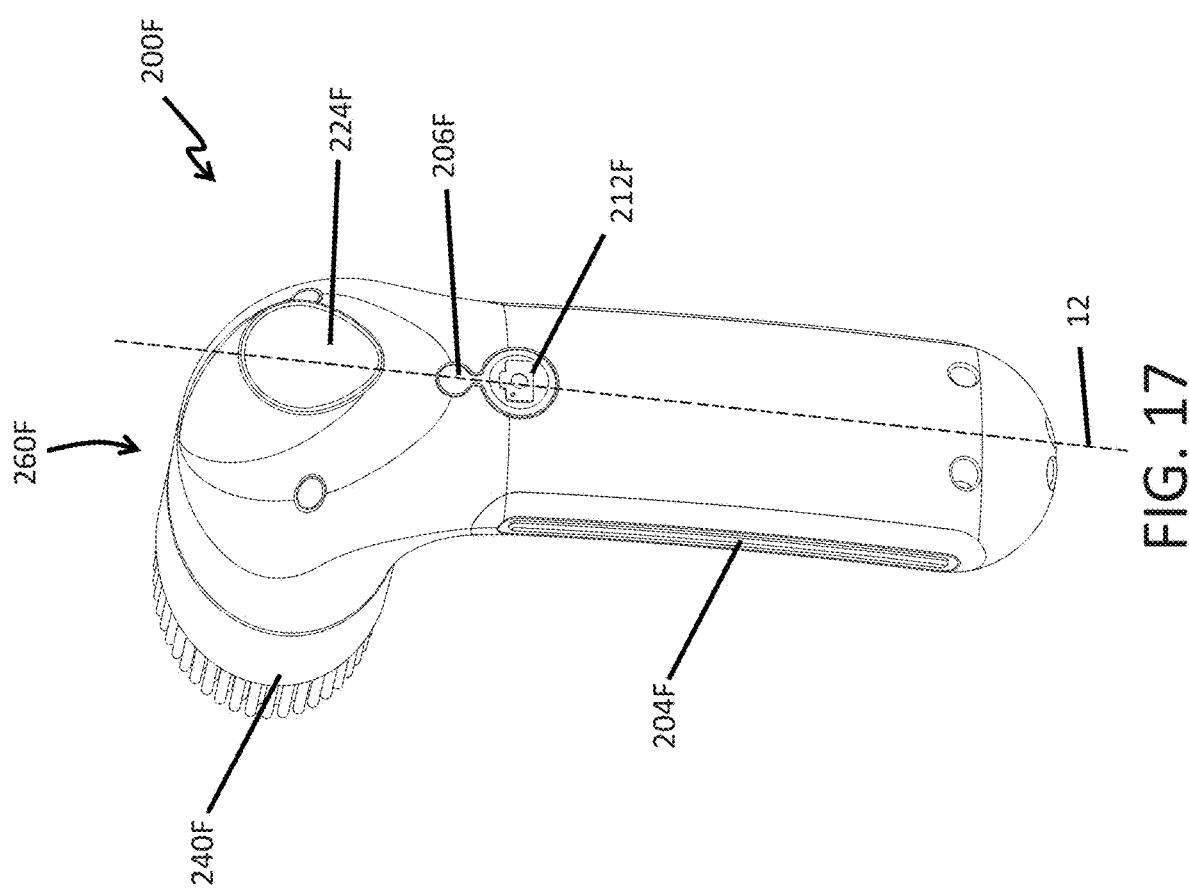
FIG. 17 shows a partial rear view of a treatment device according to some aspects of the present disclosure.

As discussed herein, the treatment head 240F can be configured to be detachable from a platform 230F of the device 200F. The platform 230F can allow a user to remove a first treatment head 240F from the device 200F and install a different treatment head 240F onto the device 200F. For example, FIG. 16A shows the device 200F with a microcurrent treatment head 240F attached to the platform 230F while FIG. 17 shows the device 200F with a brush treatment head 240F attached to the platform 230F.

In certain embodiments, the micro-current treatment head 240F can utilize microcurrent technology to trigger the body's natural skin rejuvenation mechanism. The micro current emitted at the face can be created between two poles—negative and positive that define two "lobes" or halves of a current emitter element. These lobes can be separated from one another by insulation element, which can be made from non-electrically-conductive material, such as plastic or rubber or the like. Additional embodiments and details of micro-current treatment head can be found in U.S. Pat. No. 9,272,141, which is hereby incorporated by reference herein in its entirety.

As discussed above, in some embodiments, the treatment head 240F cannot be removed from the platform 230F and/or the head portion 203F without destroying the device 200. In addition, in some embodiments, the treatment head 240F can comprise other treatment components such as a LED light device, and/or an ultrasound device. With reference to FIG. 16A, the fixed camera 222F and the treatment head 240F can be aligned with one another and face in opposite directions along the longitudinal axis 10 of the platform 230F, which in the illustrated embodiment can also be a longitudinal axis of the head portion 203F, as shown. The orientation of each of the fixed camera 222F and the treatment head 240F relative to the handle portion 202F can facilitate proper positioning of the fixed camera 222F during imaging of the skin with the device 200F and proper positioning of the treatment head 240F during treatment of the skin. As can be appreciated from FIGS. 16A and 16B, the handle portion 202F can include a gripping feature 204F that enhances the ability of the user to grip the handle portion 202F. The device 200F can include a controller 208F that allows the user to control the operation of the device 200F. The controller 208F can be positioned medially on the handle portion 202F under the treatment head 246F while the gripping features 204F are positioned laterally of the controller 208F. This arrangement of the handle portion 202F allows a user to use a thumb or finger to operate the controller 208F while the treatment head 246F is in contact with the skin. FIGS. 16A and 17 illustrate that the device 200F can include a camera control button 212F that is oriented medially on the handle portion 202F under the fixed camera 222F, thereby facilitating proper orientation of the fixed camera 222F and actuation of the fixed camera 222F without disrupting the position of the fixed camera 222F.

As discussed, the fixed camera 222F can be configured as a lens module 260F that can image or otherwise analyze the skin with or without making contact with the skin. The lens module 260F can have a cover 224F that forms a waterproof or water-resistant seal with the housing of the handle portion 202F. The cover 224F can be transparent and made of material (e.g., plastic) that allows light to pass through the cover 224F such that the lens module 260F can image the skin through the cover 224F, as described herein. In some aspects, the device 200F can include one or more sensors 243F that are configured to measure a property of the skin (e.g., elasticity, moisture content). In some aspects, the sensor 243F can measure a property of the skin when the fixed camera 222F acquires an image of the skin such that the measured property of the skin can be associated with the corresponding image of the skin. In the illustrated embodiment, the sensor 243F is disposed on the housing and adjacent the cover 224F of the lens module 260F. In some variants, the sensor 243F can be disposed on or under the cover 224F. In certain embodiments, the sensor 243F can be configured as described above with respect to sensor 243 and can be configured to provide data on skin or hair condition. For example, the sensor 243F can be configured to measure or analyze one or more of the following: moisture, pores, sebum, elasticity, fine lines, and/or wrinkles. The sensor 243F can include a capacitive sensor, an optical sensor (e.g., a photodiode), and/or an elasticity oscillating probe sensor.

FIG. 17 shows that the device 200F can include an indicator 206F. The indicator 206F can indicate a status of the device 200F, as discussed herein. In some aspects, the indicator 206F can be a LED that is mounted directly onto a PCB of the device 200F. In some aspects, the indicator 206F can be a dual-color LED light. The indicator 206F can illuminate a first color (e.g., red) to indicate a power on status of the device 206F. The indicator 206F can illuminate a second color (e.g., blue) to indicate a WiFi status of the device 206F. For example, the indicator 206F can illuminate in a steady fashion to indicate a network connection is successful. The indicator 206F can illuminate in a flashing fashion to indicate the device 200F is transferring or receiving data. The camera control button 212F can be configured to power on and off the device 200F and to operate the fixed camera 222F to take an image. For example, a press of the camera control button 212F for a prolong time (e.g., five seconds) can be used to power on or off the device 200F while a press of the button 212F for a short time (e.g., less that one second) can be used to actuate the fixed camera 222F to take an image.

As shown, the indicator 206F can be positioned relative to the camera control button 212F in such a way as to allow the user to aim the lens module 206F by feel and without looking at the device 200F. The indicator 206F can be disposed along a medial axis 12 of the device 200F between the camera control button 212F and the lens module 260F, as shown. The user can place a finger on the camera control button 212F to prepare to take an image with the fixed camera 222F. The user can feel the orientation of the indicator 206F relative to the camera control button 212F to allow the user to infer the direction of the lens module 260F without requiring the user to look at the lens module 260F. As shown, the cover 224F of the lens module 260F can have a tear-drop shape that tapers toward the indicator 206F. The tear-drop shape of the cover 224F can also help a user to aim the lens module 260F without looking at the device 200F. In some aspects, the user can feel the orientation of the tear-drop shaped cover 224F by contact of the lens module 200F with the skin. In some aspects, the user can feel the orientation of the tear-drop shaped cover with a finger of the hand that is holding the device 200F, as described herein.

Figure 18:
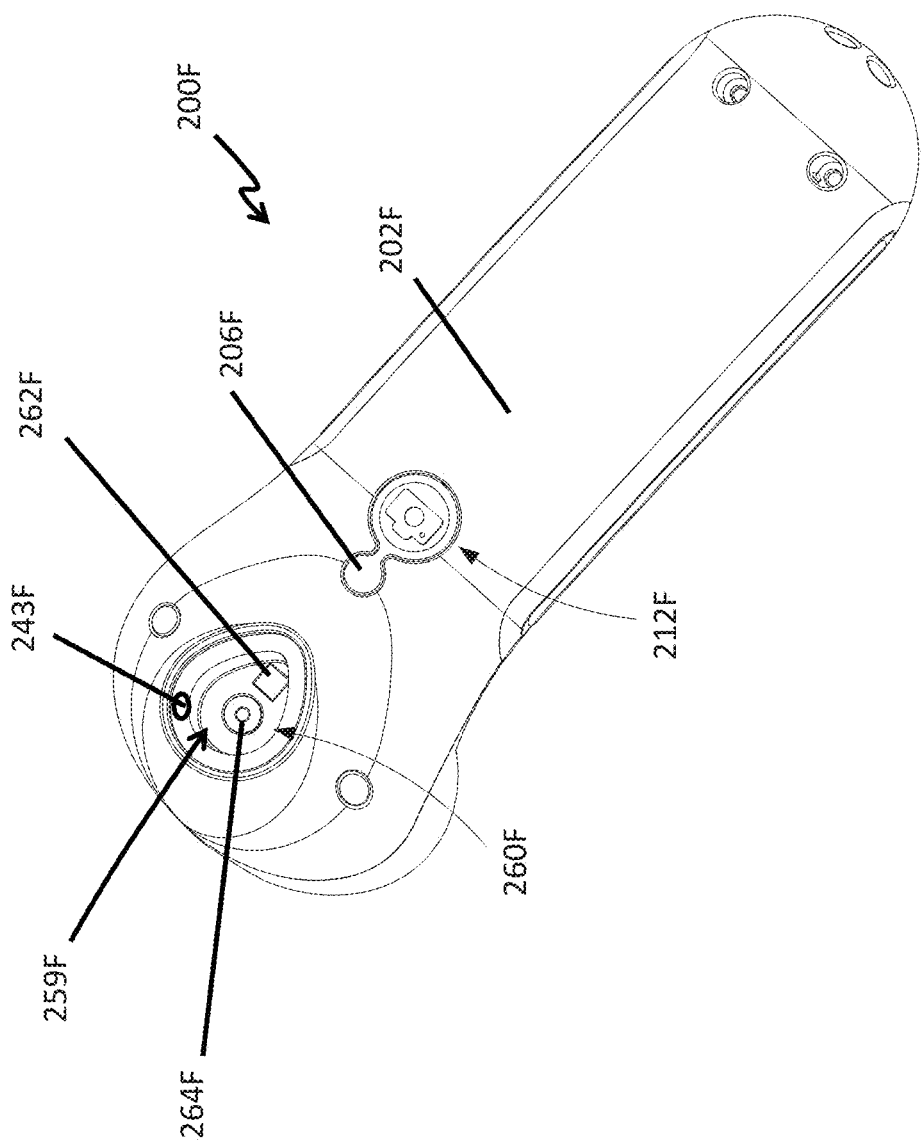
FIG. 18 shows a partial rear view of a treatment device with a cover of the lens module removed to show more clearly the internal components of the lens module.

FIG. 18 shows the device 200F with the cover 224F removed from the housing of the handle portion 202F in order to more clearly show the internal space of the lens module 260F. The lens module 260F can include a compartment 259F enclosed by the cover 224F and the housing of the handle portion 202F. As shown, the lens module 260F can include a light source 262F and a camera lens 264F. The camera lens 264F can include both an optical lens and an optical sensor that detects light after the light has passed through the optical lens. For example, in some variants the camera lens 264F can be an optical lens that is arranged in series with an optical sensor (e.g., 2 mega-pixel sensor, 1920×1080). The light source 262F and the camera lens 264F can each be disposed under the cover 224F (e.g., within the compartment 259F) such that the light source 262F can illuminate the skin for the camera lens 264F whether the cover 224F is in contact with the skin or spaced apart from the skin. In this way, the lens module 260F can enable dual modes of skin imaging or analysis. In some aspects, a sensor 243F can be positioned under the cover 224F. The sensor 243F can be configured to measure a characteristic of the skin (e.g., elasticity). In some aspects, the sensor 243F can measure the skin when the cover 224F is in contact with the skin (e.g., elasticity). In some aspects, the sensor 243F can measure a skin characteristic when the cover 224F is spaced apart from the skin (e.g., infrared thermal properties). In some aspects, the light source can be an LED. In some aspects, the light source 262F can be a super luminosity white LED. In some aspects, the light source 262F can be a flashlight for a digital camera or cellular phone.

Figure 19:
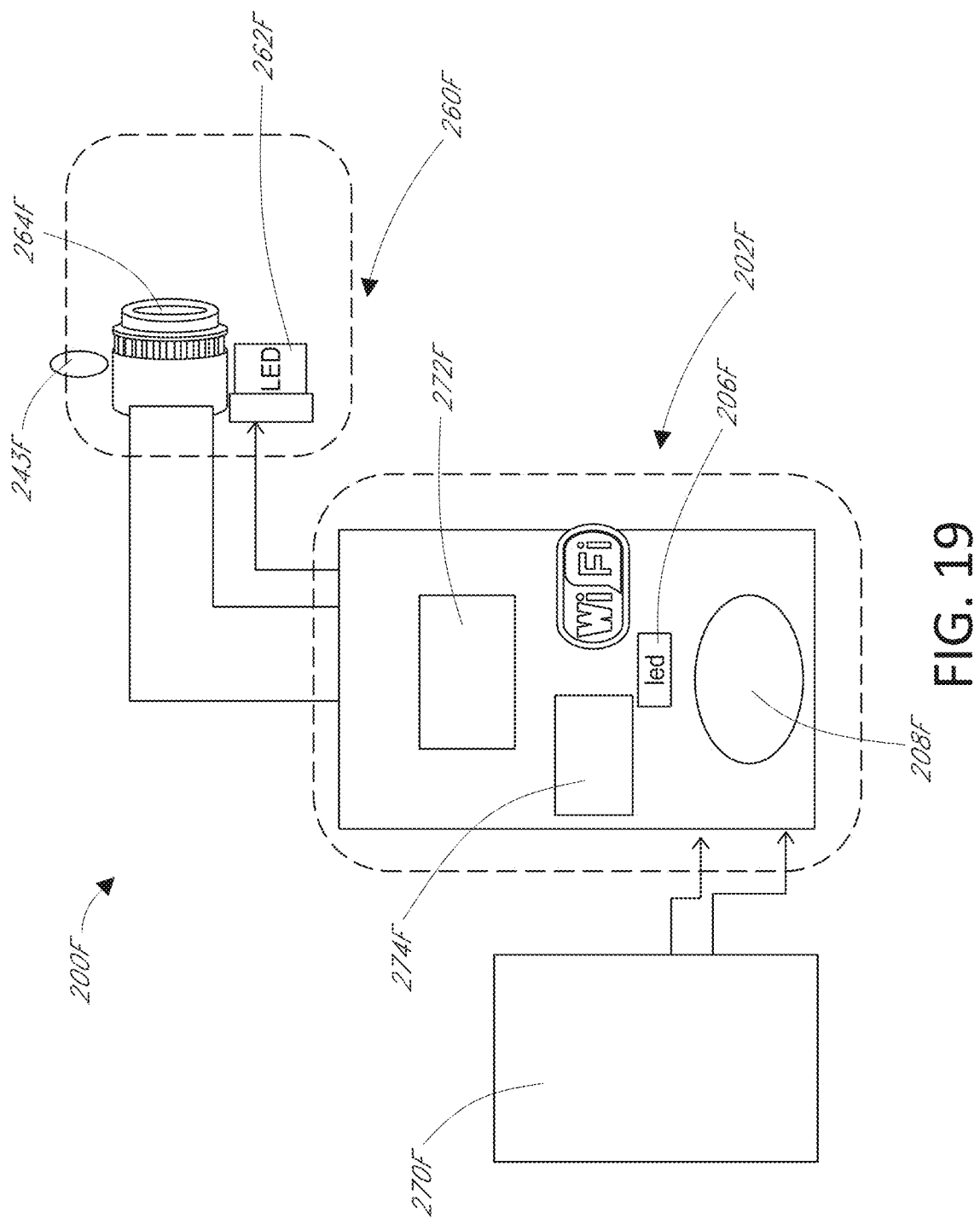
FIG. 19 is a schematic representation of the arrangement of a treatment device according to some aspects of the present disclosure.

FIG. 19 is a schematic illustration of a hardware of the device 200. The device 200F can include a battery 270F. The battery 270F can be rechargeable or disposable. The device 200F can include a main board 272F. The main board 272F can be connected to the battery 270F. The main board 272F can receive an input from one or more of the controller 108, the camera control button 212F, the sensor 243F, and the camera lens 264F. The device 200F can include a memory 274F (e.g., flash drive). The indicator 206F can be wired directly to the main board 272F. The main board 272F can be wired to the light source 262F and the camera lens 264F.

Figure 20:
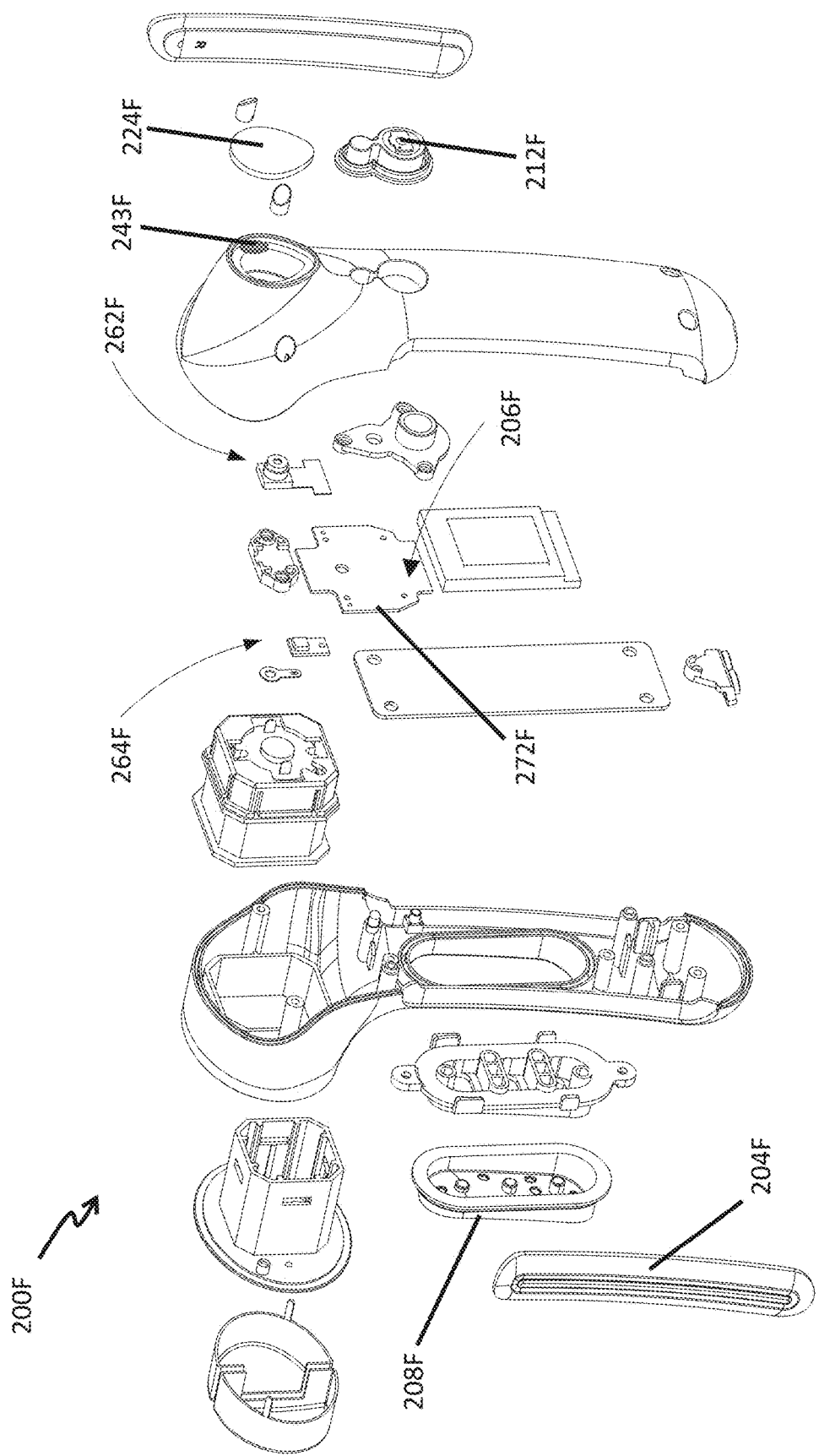
FIG. 20 is an exploded view of a treatment device according to some aspects of the present disclosure.

FIG. 20 shows an exploded view of the device 200. As discussed, the main board 272F can be connected directly or indirectly to one or more of the indicator 206F, the light source 262F, and the camera lens 264F. The main board 272F can receive an input from one or more of the controller 208F, the camera control button 212F, the camera lens 264F, and the sensor 243F.

Figure 21:
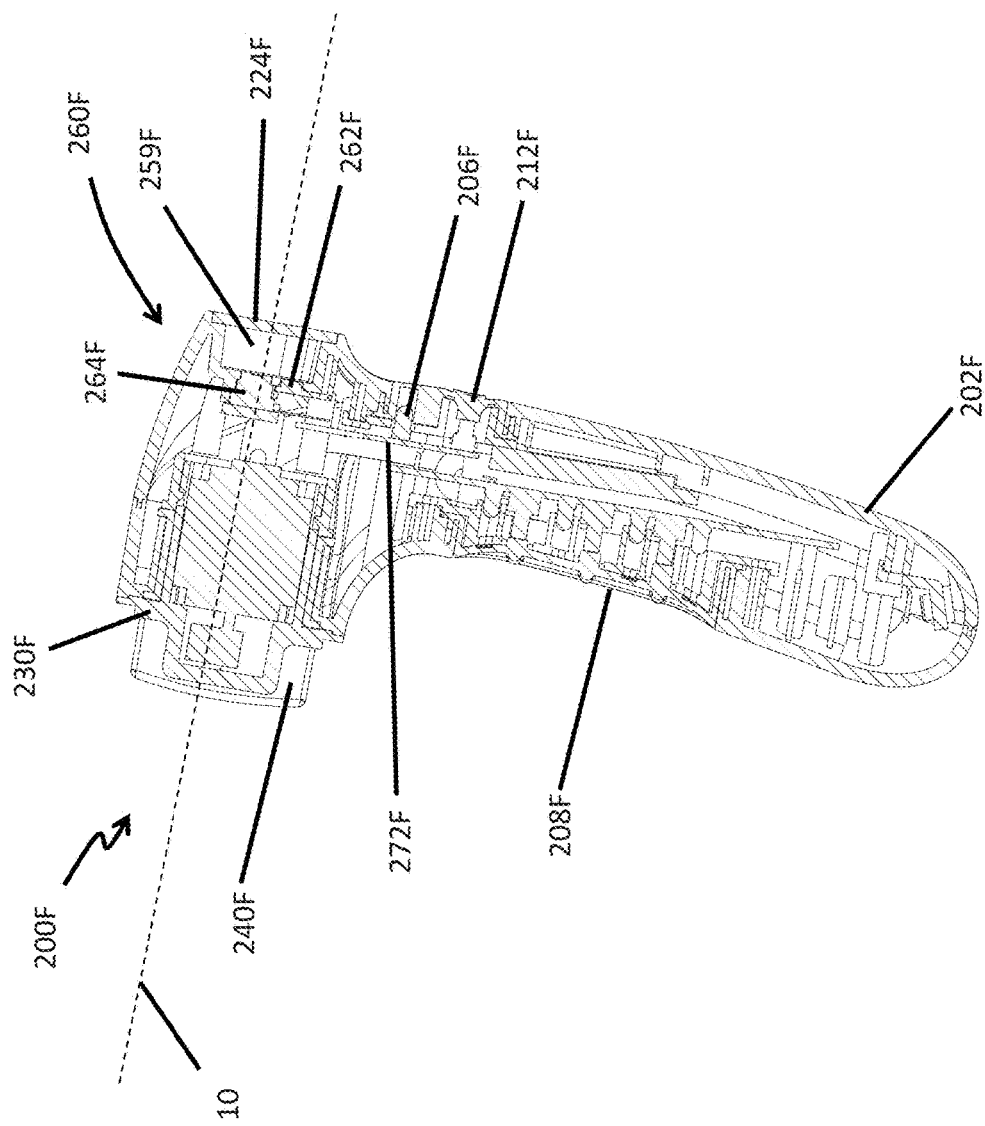
FIG. 21 is a side cross-sectional view of a treatment device according to some aspects of the present disclosure.

FIG. 21 illustrates a side cross-sectional view of the device 200F. As discussed, the lens module 260F and the treatment head 240F can be longitudinally aligned with one another along the longitudinal axis of the platform 230F. The light source 262F and the camera lens 264F can be enclosed by the housing of the head portion 203F and the cover 224F of the lens module 260F. The controller 208F and the camera control button 212F can be positioned on the handle portion 202F such that a user can orient the treatment head 240F or the lens module 260F without requiring the user to look at the device 200F, as discussed herein. The lens module 260F can be configured to image or otherwise analyze the skin in either a mode in which the device 200F is contacting the skin or in a mode in which the device 200F is not contacting the skin.

Figure 22:
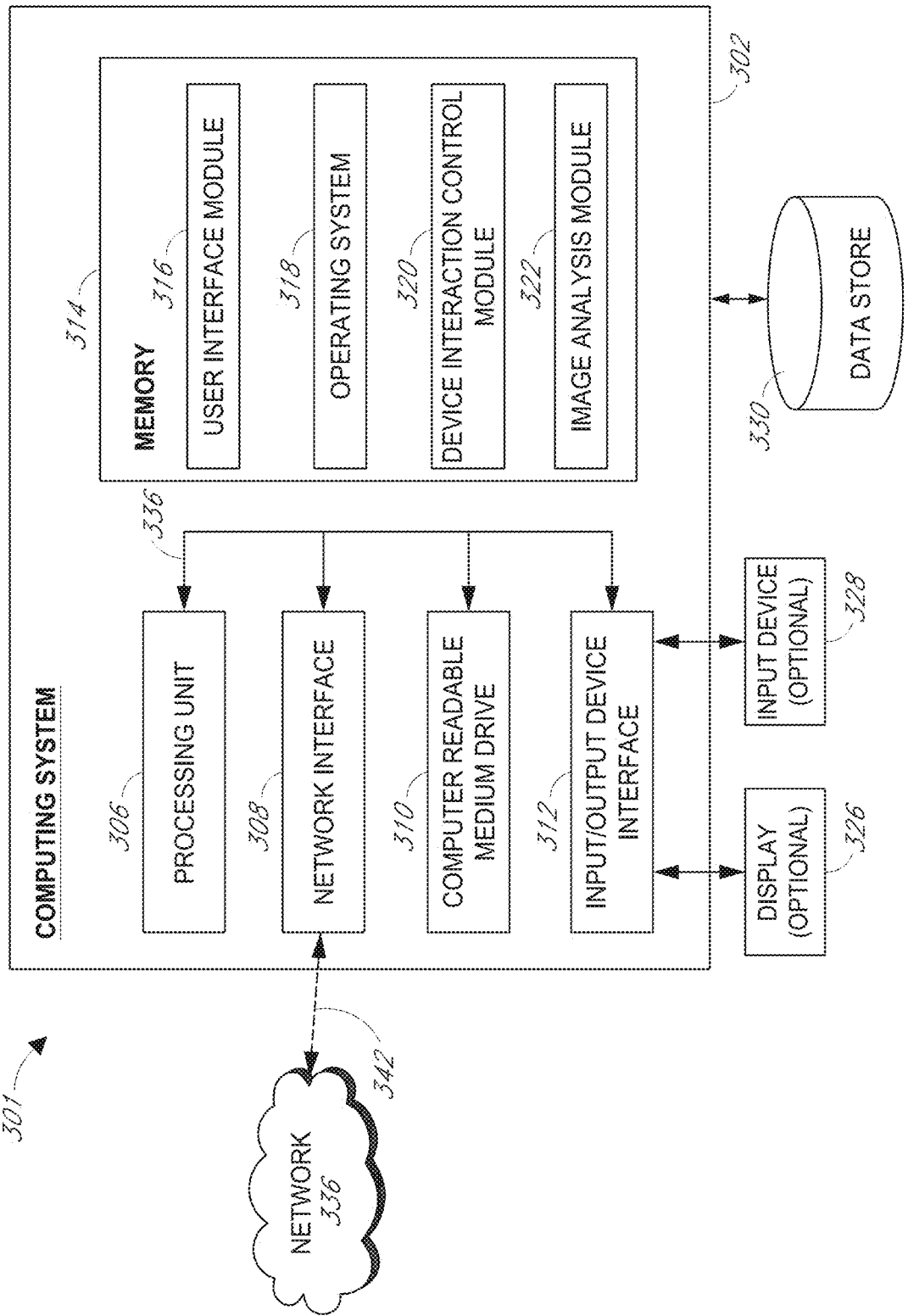
FIG. 22 is a system block diagram of a computing system suitable for use in various embodiments of the present disclosure.

FIG. 22 illustrates certain components of a computing environment 301 suitable for use in various embodiments of the present disclosure, with further components discussed above with respect to FIG. 1. As depicted in FIG. 22, the computing environment 301 may include a computing system 302. The general architecture of the computing system 302 may include an arrangement of computer hardware and software components used to implement aspects of the present disclosure. The computing system 302 may include many more (or fewer) elements than those shown in FIG. 22. It is not necessary, however, that all of these generally conventional elements be shown in order to provide an enabling disclosure. In some embodiments, the computing system 302 may be an example of what is referred to as the mobile device 400 above. The device 200 described above may additionally or alternatively include similar hardware to that illustrated as being included in computing system 302, such as a display, processing unit, network interface, memory, operating system, etc. Furthermore, modules illustrated as part of computing system 302 (such as device interaction and control module 320 and image analysis module 322) may be included within mobile device 400, device 200, and/or another remote or local device, depending on the embodiment.

As illustrated, the computing system 302 includes a processing unit 306, a network interface 308, a computer readable medium drive 310, an input/output device interface 312, an optional display 326, and an optional input device 328, all of which may communicate with one another by way of a communication bus 336. The processing unit 306 may communicate to and from memory 314 and may provide output information for the optional display 326 via the input/output device interface 312. The input/output device interface 312 may also accept input from the optional input device 328, such as a keyboard, mouse, digital pen, microphone, touch screen, gesture recognition system, voice recognition system, or other input device known in the art. In some embodiments, the input-output device interface 312 or network interface 308 may be used to communicate with the device 200 described above.

The memory 314 may contain computer program instructions (grouped as modules or components in some embodiments) that the processing unit 306 may execute in order to implement one or more embodiments described herein. The memory 314 may generally include RAM, ROM and/or other persistent, auxiliary or non-transitory computer-readable media. The memory 314 may store an operating system 318 that provides computer program instructions for use by the processing unit 306 in the general administration and operation of the computing system 302. The memory 314 may further include computer program instructions and other information for implementing aspects of the present disclosure. For example, in one embodiment, the memory 314 may include a user interface module 316 that generates user interfaces (and/or instructions therefor) for display upon a computing system, e.g., via a navigation interface such as a browser or application installed on the computing system 302 or the client computing system 303.

In some embodiments, the memory 314 may include a device interaction and control module 320 and image analysis module 322, which may be executed by the processing unit 306 to perform operations according to various embodiments described herein. For example, the device interaction and control module 320 may be used to send control commands to the device 200, while the image analysis module 322 may be configured to analyze image data or images received from the device 200. The modules 320 and/or 322 may access the data store 330 in order to retrieve data described above and/or store data (such as images and associated metadata). The data store may be part of the computing system 302, remote from the computing system 302, and/or may be a network-based service.

In some embodiments, the network interface 308 may provide connectivity to one or more networks or computing systems, and the processing unit 306 may receive information and instructions from other computing systems or services via one or more networks. In particular, the computing system 302 may establish a communication link 342 with a network 336 (e.g., using known protocols) in order to send communications to other devices over the network 336.

CONCLUSION

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

The various illustrative modules, API features, computer functionality, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system in a given embodiment. The described functionality can be implemented in varying ways for each particular application, but such implementation decisions should not be interpreted as causing a departure from the scope of the disclosure.

What is claimed is:
1. A skin evaluation system configured to receive image data and sensor data from a device placed near a skin region of interest, the skin evaluation system comprising:
   computer-readable memory storing executable instructions; and
   one or more processors in communication with the computer-readable memory and configured by the executable instructions to:
      receive the image data and the sensor data via a network interface, wherein the image data represents the skin region of interest;
      evaluate the image data and the sensor data using a neural network machine learning model to generate skin evaluation results representing a measurement of a condition of the skin region of interest; and evaluate the skin evaluation results using a further machine learning model to generate treatment results representing a treatment for the condition of the skin region of interest.

2. The skin evaluation system of claim 1, wherein the measurement of the condition of the skin region of interest is selected from a group consisting of: a skin feature size, a skin feature depth, and a presence of debris.

3. The skin evaluation system of claim 1, wherein the sensor data represents a characteristic of the skin region of interest.

4. The skin evaluation system of claim 3, wherein the characteristic of the skin region of interest is selected from a group consisting of: a moisture content and a secretion amount.

5. The skin evaluation system of claim 1, wherein the neural network machine learning model comprises a convolutional neural network.

6. The skin evaluation system of claim 1, wherein the one or more processors are further configured by the executable instructions to present the image data on a display in substantially real time.

7. The skin evaluation system of claim 1, wherein the one or more processors are further configured by the executable instructions to:
compare the image data with prior image data, wherein the prior image data represents the skin region of interest at a point in time preceding generation of the image data; and
evaluate a change in the skin region of interest based on comparing the image data with the prior image data.

8. The skin evaluation system of claim 1, wherein the neural network machine learning model is configured to assess an extent of damage of the condition of the skin region of interest.

9. The skin evaluation system of claim 1, wherein the one or more processors are further configured by the executable instructions to recommend a device setting for use of the device based on output of at least one of the neural network machine learning model or the further machine learning model.

10. The skin evaluation system of claim 1, further comprising the device configured to be placed near the skin region of interest.

11. The skin evaluation system of claim 10, wherein the device configured to be placed near the skin region of interest comprises a light source configured to administer light therapy to the skin region of interest.

12. The skin evaluation system of claim 10, wherein the device further comprises at least one of: a moisture sensor, a capacitive sensor, a photodiode optical sensor, or an elasticity oscillating probe sensor.

13. A computer-implemented method for processing image data and sensor data from a device placed near a skin region of interest, the computer-implemented method comprising:
under control of a computing system comprising a computer processor configured to execute specific instructions:
receiving the image data and the sensor data via a network interface from the device, wherein the image data represents the skin region of interest;
evaluating the image data and the sensor data using a neural network machine learning model to generate skin evaluation results representing a measurement of a condition of the skin region of interest; and
evaluating the skin evaluation results using a further machine learning model to generate treatment results representing a treatment for the condition of the skin region of interest.

14. The computer-implemented method of claim 13, wherein the measurement of the condition of the skin region of interest is selected from a group consisting of: a skin feature size, a skin feature depth, and a presence of debris.

15. The computer-implemented method of claim 13, wherein the sensor data represents a characteristic of the skin region of interest.

16. The computer-implemented method of claim 15, wherein the characteristic of the skin region of interest is selected from a group consisting of: a moisture content and a secretion amount.

17. The computer-implemented method of claim 13, further comprising presenting the image data on a display in substantially real time.

18. The computer-implemented method of claim 13, further comprising:
comparing the image data with prior image data, wherein the prior image data represents the skin region of interest at a point in time preceding generation of the image data; and
evaluating a change in the skin region of interest based on comparing the image data with the prior image data.

19. The computer-implemented method of claim 13, wherein the neural network machine learning model is configured to assess an extent of damage of the condition of the skin region of interest.

20. The computer-implemented method of claim 13, further comprising recommending a device setting for use of the device based on output of at least one of the neural network machine learning model or the further machine learning model.

* * * * *